(12) United States Patent
Yonezawa et al.

(10) Patent No.: US 8,504,167 B2
(45) Date of Patent: Aug. 6, 2013

(54) LIVING TISSUE STIMULATION CIRCUIT

(75) Inventors: Eiji Yonezawa, Okazaki (JP); Kenzo Shodo, Kyoto (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/289,440

(22) Filed: Nov. 4, 2011

(65) Prior Publication Data
US 2012/0116483 A1 May 10, 2012

(30) Foreign Application Priority Data

Nov. 5, 2010 (JP) .................................. 2010-249173
Dec. 2, 2010 (JP) .................................. 2010-269108

(51) Int. Cl.
*A61N 1/08* (2006.01)
(52) U.S. Cl.
USPC .................................. 607/74; 607/36; 607/37

(58) Field of Classification Search
USPC .............................................. 607/36, 37, 74
See application file for complete search history.

(56) References Cited

FOREIGN PATENT DOCUMENTS
JP 2010-187747 A 9/2010

*Primary Examiner* — Joseph Dietrich
(74) *Attorney, Agent, or Firm* — Sughrue Mion, PLLC

(57) ABSTRACT

A living tissue stimulation circuit includes: an H-bridged circuit that includes a first series section in which a first semiconductor switch connected to a power source side and a third semiconductor switch connected to a ground side are connected to each other in series, and a second series section in which a second semiconductor switch connected to the power source side and a fourth semiconductor switch connected to the ground side are connected to each other in series, the first series section and the second series section being connected to each other in parallel; a stimulation electrode connected to a first node between the first and third semiconductor switches; a counter electrode connected to a second node between the second and fourth semiconductor switches; and a current adjusting circuit configured to determine a current value output from the stimulation electrode.

12 Claims, 14 Drawing Sheets

US 8,504,167 B2

LIVING TISSUE STIMULATION CIRCUIT

BACKGROUND

The present invention relates to a living tissue stimulation circuit that applies an electrical stimulation to a part of a living tissue.

An electrical stimulation device has been studied which adjusts functions of a living body by embedding a stimulation electrode (hereinafter, referred to as an electrode) in a living body and electrically stimulating a part of the living body. Examples of such an electrical stimulation device include an artificial middle ear delivering the vibration of sound to a patient's auditory ossicle and a heart pacemaker being embedded in a patient's chest to suppress an occurrence of irregular heartbeat by applying an electrical stimulation to a heart. A vision regeneration assisting apparatus has been also known which promotes the regeneration of vision by electrically stimulating cells of the retina with an electrical stimulation pulse signal (charge) output from an electrode (JP2010-187747).

In applying an electrical stimulation to the living tissue through the use of such an electrical stimulation device, it is necessary to inject a predetermined amount of charge into cells from an electrode so as to supply the stimulation necessary for the cells. An electrical stimulation pulse signal corresponding to a feeling of stimulation and being output from the electrode is a bipolar electrical stimulation pulse signal (hereinafter, referred to as a bipolar pulse) having amplitudes in the positive and negative (+ and −) directions. The positive and negative (+ and −) polarities of the bipolar pulse are switched through the use of plural semiconductor switches. By switching the polarity of charge (current), the deflection of charge in an electrically-stimulated site is reduced and thus the charge balance is maintained. The electrical stimulation on the living body is suitably carried out.

SUMMARY

However, in the related living tissue stimulation circuit, the following problem is caused depending on stimulation conditions of the bipolar pulse. That is, when the polarity of current of the bipolar pulse is changed, the parasitic PN junction of the semiconductor switch which should be originally turned off is forward biased and thus uncontrollable current flows in the circuit. Accordingly, when the balance of positive and negative (+ and −) charges is broken down and deflected, the charge left in the living body badly influences a patient's living tissue.

Accordingly, it is necessary to limit the stimulation conditions of the bipolar pulse to stimulation conditions under which the parasitic PN junction of a semiconductor switch to be turned off is not forward biased and the positive and negative (+ and −) charge balance is maintained.

An object of the invention is to provide a living tissue stimulation circuit which can broaden the setting range of stimulation conditions of a bipolar pulse to more suitably apply the electrical stimulation to the living tissue.

To achieve the above-mentioned object, an aspect of the invention provides the following configurations.

(1) A living tissue stimulation circuit comprising:

an H-bridged circuit that includes a first series section in which a first semiconductor switch connected to a power source side and a third semiconductor switch connected to a ground side are connected to each other in series, and a second series section in which a second semiconductor switch connected to the power source side and a fourth semiconductor switch connected to the ground side are connected to each other in series, the first series section and the second series section being connected to each other in parallel;

a stimulation electrode connected to a first node between the first semiconductor switch and the third semiconductor switch of the first series section;

a counter electrode connected to a second node between the second semiconductor switch and the fourth semiconductor switch of the second series section; and a current adjusting circuit configured to determine a current value output from the stimulation electrode, the current adjusting circuit including a first current source disposed at an end of the ground side of the third semiconductor switch and an end of the ground side of the fourth semiconductor switch and a second current source disposed at an end of the power source side of the first semiconductor switch and an end of the power source side of the second semiconductor switch.

(2) The living tissue stimulation circuit according to (1), wherein a bypass switch connected in parallel to the first current source or the second current source so as to bypass the first current source or the second source and the H-bridged circuit is disposed in at least one of the power source side and the ground side.

(3) The living tissue stimulation circuit according to (2), wherein the bypass switch is connected in parallel to the first semiconductor switch and the third semiconductor switch or is connected in parallel to the second semiconductor switch and the fourth semiconductor switch.

(4) The living tissue stimulation circuit according to (3), wherein a combination of the first semiconductor switch and the fourth semiconductor switch and a combination of the second semiconductor switch and the third semiconductor switch of the H-bridged circuit are alternately turned on and off so as to switch positive and negative current polarities of a first pulse and a second pulse of a bipolar electrical stimulation pulse output from the stimulation electrode.

(5) The living tissue stimulation circuit according to (4), wherein the current polarity of the bipolar electrical stimulation pulse signal is switched to any one of an anodic-first pattern in which positive current is output in the first pulse and negative current is output in the second pulse and a cathodic-first pattern in which negative current is output in the first pulse and positive current is output in the second pulse.

(6) The living tissue stimulation circuit according to (5), wherein at least one of the bypass switches connected in parallel to the first current source and the second current source is turned on when the first pulse is output and is turned off when the second pulse is output.

(7) The living tissue stimulation circuit according to (6) further comprising a potential difference detection circuit configured to detect a potential difference between the first node and the second node, wherein at least one of the bypass switches connected in parallel to the first current source and the second current source is turned on depending on the potential difference detected by the potential difference detection circuit.

(8) A living tissue stimulation circuit comprising:

an H-bridged circuit that includes a first series section in which a first semiconductor switch connected to a power source side and a third semiconductor switch connected to a ground side are connected to each other in series, and a second series section in which a second semiconductor switch connected to the power source side and a fourth semiconductor switch connected to the ground side are connected to each other in series, the first series section and the second series section being connected to each other in parallel;

a stimulation electrode connected to a first node between the first semiconductor switch and the third semiconductor switch of the first series section;

a counter electrode connected to a second node between the second semiconductor switch and the fourth, semiconductor switch of the second series section; and a potential compensation circuit configured to adjust the potential of at least one of the first node and the second node so as to satisfy a voltage range in which a parasitic PN junction of the semiconductor switch to be turned off is not forward biased.

(9) The living tissue stimulation circuit according to (8), wherein the potential compensation circuit includes a detection circuit configured to detect the potential of at least one of the first node and the second node.

(10) The living tissue stimulation circuit according to (9), wherein when the detection circuit is connected to both the first node and the second node, the detection circuit detects an average potential, of the first node and the second node or a higher or lower potential of the potentials of the first node and the second node.

(11) The living tissue stimulation circuit according to (10), wherein the potential compensation circuit is a bootstrap circuit.

(12) The living tissue stimulation circuit according to (11), wherein the potential compensating circuit includes:

a rectifier circuit connected to the power source side; and a capacitor connected to the rectifier circuit and one of the first semiconductor switch and the second semiconductor switch of the power source side, the capacitor being charged with the potential with one polarity of a bipolar pulse, and the charged potential of the capacitor becomes higher than the potential of the power source side due to the polarity inversion of the bipolar pulse and the first semiconductor switch or the second semiconductor switch is prevented from being forward biased due to the potentials of the first node and the second node.

DESCRIPTION OF EXEMPLARY EMBODIMENTS

Figure 1:
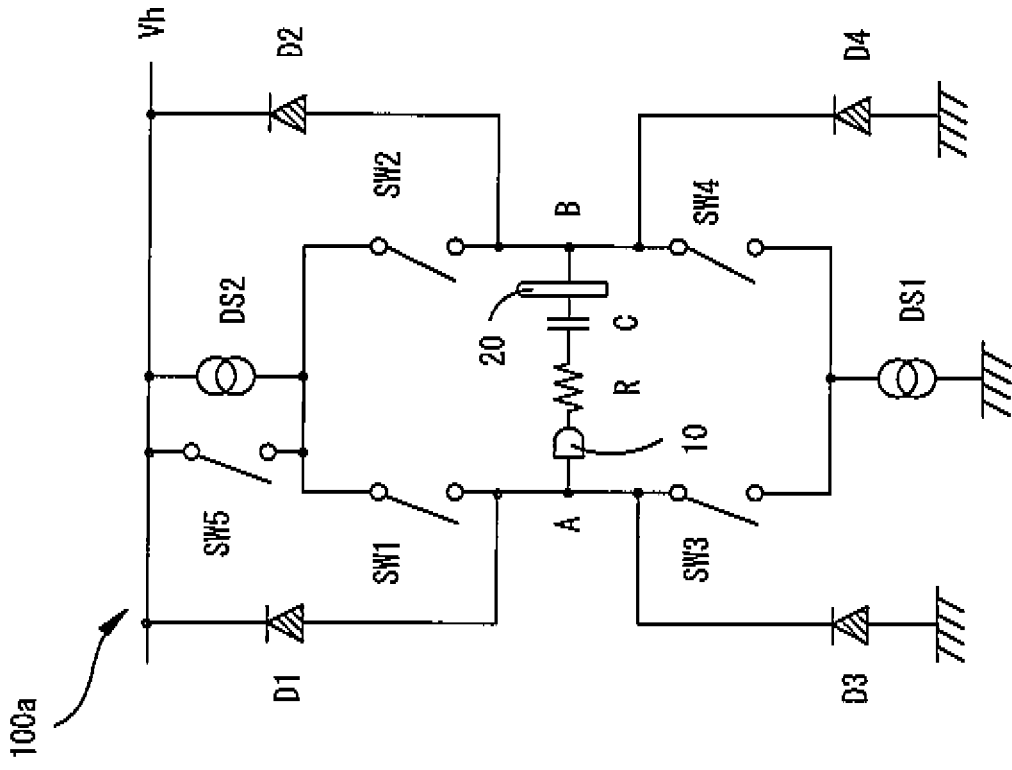
FIG. 1 is a diagram illustrating a living tissue stimulation circuit including a current adjusting circuit.

FIG. 1 is a circuit block diagram of a living tissue stimulation circuit (hereinafter, referred to as a stimulation circuit) 100. The stimulation circuit 100 includes an H-bridged circuit having four MOS transistor switches (hereinafter, referred to as switches) SW1 to SW4 formed of n-MOS (or p-MOS) as semiconductor switches, a stimulation electrode (electrode) 10 connected to a node A serving as an output terminal of the H-bridged circuit, a counter electrode 20 connected to a node B serving as another output terminal, a DC positive (+) current source (hereinafter, referred to as a current source) DS1 connected to a ground side so as to limit current output from the electrode 10 to a constant current value, and a DC positive (+) current source (hereinafter, referred to as a current source) DS2 connected to a source Vh side.

For the purpose of explanation, it is shown in FIG. 1 that parasitic diodes D1 to D4 unique to the switches SW1 to SW4 are in parallel to the switches SW1 to SW4. The respective current sources are formed of a mirror circuit. The mirror circuit includes bipolar or MOS transistors or the like. For example, in this embodiment, p-MOS transistors and n-MOS transistors are used.

In the H-bridged circuit (polarity switching circuit), an end of the switch SW1 and an end of the switch SW2 are connected to the current source DS2 connected to the source (line) Vh. An end of the switch SW3 and an end of the switch SW4 are connected to the current source DS1 connected to the ground side. The other end of the switch SW1 and the other end of the switch SW3 are connected in series to each other and the node A is formed at the connection position thereof. The other end of the switch SW2 and the other end of the switch SW4 are connected in series to each other and the node B is formed at the connection position thereof. The node A is connected to the electrode 10 used to electrically stimulate a patient's living tissue and the node B is connected the counter electrode 20.

In the H-bridged circuit having the above-mentioned configuration, a combination of opposing switches (a combination of SW1 and SW4 or a combination of SW2 and SW3) forms a pair and performs the same operation. On the other hand, the switches of the different combinations perform the reverse operations. By alternately switching the ON and OFF states of the combinations of opposing switches, the current source DS1 and the current source DS2 are driven on the basis of the voltage supplied from a single power source Vh. Accordingly, the positive and negative (+ and −) polarities of the current output from the electrode 10 are alternately inverted. A living tissue is electrically stimulated by a bipolar electrical stimulation pulse signal (hereinafter, referred to as a bipolar pulse) output from the electrode 10.

In this embodiment, the positive and negative (+ and −) charge balance of the bipolar pulse output from the electrode 10 is maintained regardless of the stimulation conditions of the bipolar pulse through the use of a current adjusting circuit including the current source DS1 connected to the ground side and the current source DS2 connected to the power source Vh side. The principle of maintaining the charge balance of the bipolar pulse through the use of the current adjusting circuit including two current sources will be described in detail later.

A stimulated circuit including a living tissue is disposed between the node A and the node B of the stimulation circuit 100. The electrical characteristic of the stimulated circuit (the living tissue) is expressed by a series connection of a capacitive component Ce generated in an electrical double layer formed on the surface of the electrode 10, a resistive component Re unique to the living body, a DC blocking capacitor Co used to determine an effective voltage range and to suitably cut a DC component, and an output resistor Ro of the stimulation circuit 100. In FIG. 1, the above-mentioned electrical characteristic of the stimulated circuit is simplified as a series connection of an equivalent capacitor C (Ce+Co) and an equivalent resistor R (Re+Ro).

Since the capacitance of the capacitor Co assembled into the stimulation circuit 100 can be made to be sufficiently great, the potential of the equivalent capacitor C is substantially determined depending on the capacitive component Ce generated in the electrical double layer. The capacitive component Ce is determined depending on the surface area of the electrode 10 and the state of the living body to be stimulated.

The operation of the living tissue stimulation circuit 100 will be described below. Here, an application pattern (cathodic-first pattern) in which current (negative (−) current) is made to flow in the stimulation electrode via the living body from the counter electrode 20 at first (in the first pulse), then current (positive (+) current) is made to flow in the counter electrode 20 via the living body from the stimulation electrode 10 with the switched polarity (in the second pulse) will be exemplified as the bipolar pulse.

First, the combination of the switch SW2 and the switch SW3 is turned on and the combination of the switch SW1 and the switch SW4 is turned off in response to an instruction signal from a controller (not shown) connected to the stimulation circuit 100. In this case, the node B becomes the potential of the power source Vh side and the node A becomes the potential of the ground side due to the current source DS1. Accordingly, negative (−) stimulation pulse current (negative (−) current) is output from the electrode 10 (the first pulse). The capacitor C is charged with the negative (−) current to have a predetermined potential.

Then, by causing positive (+) current having the opposite polarity and the same amount of charge as the negative (−) current to flow, the controller switches the combination of the switch SW2 and the switch SW3 to the OFF state and switches the combination of the switch SW1 and the switch SW4 to the ON state. Accordingly, the node A becomes the potential of the power source Vh side and the node B becomes the potential of the ground side due to the current source DS1. Accordingly, positive (+) stimulation pulse current (positive (+) current) is output from the electrode 10 (the second pulse).

On the other hand, in inverting the polarity of the current output from the electrode 10, when the potential Vr of voltage drop clue to the resistor R at the time of applying the second pulse (the positive (+) stimulation pulse in this case) is lower than the potential Vc of the capacitor C charged with the first pulse (the negative (−) stimulation pulse in this case), the potential of the node B becomes higher than the potential of the node A in the moment of inverting the polarity of the current.

At this time, when the current value of the current source DS2 is greater (slightly greater) than the current value of the current source DS1, the potentials of the node A and the node B are drawn to the power source Vh and the parasitic diode D2 is thus turned on. Accordingly, the current difference between the current source DS2 and the current source DS1 flows in the current source DS2. On the other hand, when the current value of the current source DS2 is smaller (slightly smaller) than the current value of the current source DS1, the potentials of the node A and the node B are attracted to the ground potential and the parasitic diode D3 is thus turned on. Accordingly, the current difference between the current source DS2 and the current source DS1 flows in the parasitic diode D3.

That is, in any case, the current value of the current flowing in the parasitic diode corresponds to the difference between the current value of the current source DS1 and the current value of the current source DS2. Therefore, by selecting current sources having no practical problem with a current difference as the current source DS1 and the current source DS2, desired current can be made to flow from the stimulation circuit 10.

Figure 5:
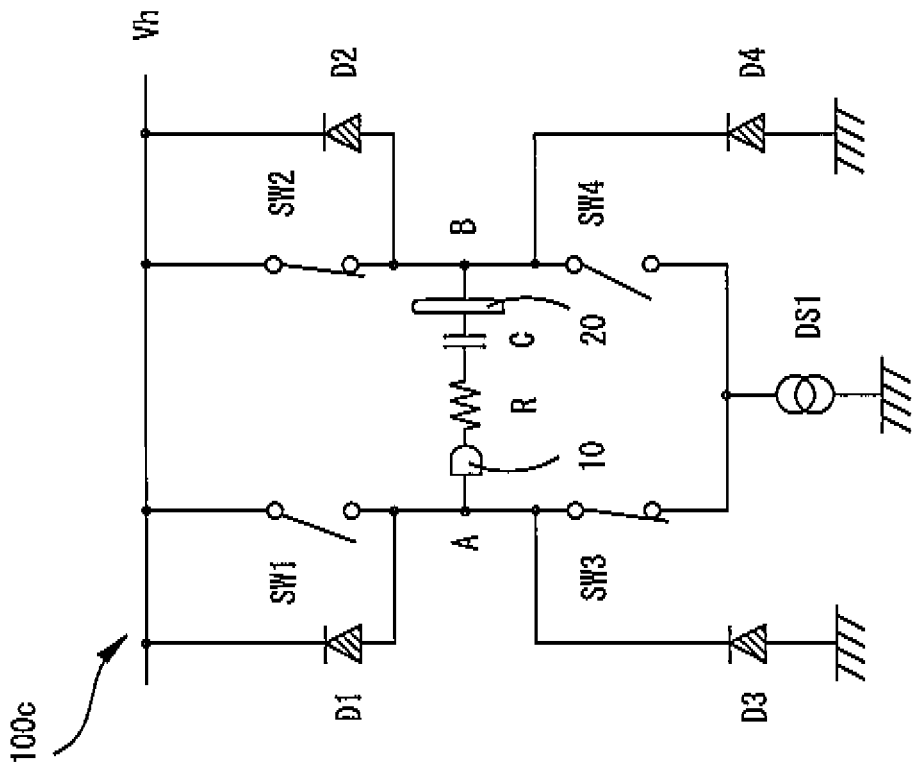
FIG. 5 is a circuit diagram illustrating a living tissue stimulation circuit according to the background art.

Here, the stimulation circuit 100c according to the background art is shown in FIG. 5 and a problem with generation of improper current will be described in detail. The stimulation circuit 100c has a configuration in which the current source DS2 is removed from the stimulation circuit shown in FIG. 1 and the end of the switch SW1 and the end of the switch SW2 are connected in series to the power source (line) Vh. In the stimulation circuit 100c, when the parasitic diode (PN junction) D2 of the switch SW2 is forward biased (turned on) in inverting the polarity of the stimulation current, an improper path d (the diode D2→the switch W1→the node A→the living tissue→the node B) in which current flows from the parasitic diode D2 to the power source Vh is formed.

At this time, since the improper path d does not include the current source DS1, the current of the improper path d cannot be controlled by the current source DS1. As a result, current greater than the value of the stimulation current determined by the current source DS1 is output from the electrode 10. Accordingly, when the charge balance of the current applied to the living tissue is broken down and the charge is accumulated in the living body, the patient's living body may be badly influenced such as electrolysis of body fluids. Particularly, when such a stimulation condition of the bipolar pulse that the current value of the second pulse is lower than the current value of the first pulse is set, the potential Vr of voltage drop in the resistor R in outputting the second pulse is reduced and greater improper current can be easily generated.

Therefore, in this embodiment, the current source DS2 is connected between the power source Vh and the witches SW1 and SW2 where the improper path may be formed. Accordingly, even when an improper path is formed in the circuit, the current necessarily flows via the current source DS1 or the current source DS2 and is limited to the current value determined by the current source DS1 or DS2.

When the current source DS1 and the current source DS2 have a completely identical characteristic (current value), the improper current is not made to flow in the circuit. However, a difference (error) is typically present between the current value of the current source DS1 and the current value of the current source DS2. Therefore, in this embodiment, the current source DS1 and the current source DS2 are selected so that the difference between the current values thereof is in the margin of error of the stimulation current. As a result, even when the improper current flows in the stimulation circuit 100, the current value is suppressed within the margin of error of the stimulation current value, whereby the charge balance of the bipolar pulse is maintained.

The stimulation circuit 100 according to this embodiment will be described again with reference to FIG. 1. As described above, when the first pulse is output from the electrode 10 and then the potential of the node B then becomes higher than the potential of the power source Vh (the node A) with the inversion in polarity of the current by the switching of the switches, the parasitic diode D2 to be originally turned of is forward biased to form an improper path. The improper path formed in the stimulation circuit 100 is formed on the side with a greater output current value, by comparing the output current values of the current source DS1 and the current source DS2 with each other.

For example, when the current value of the current source DS2 is greater, the improper path is formed as a path (the capacitor C→the diode D2→the current source DS2→the switch SW1→the resistor R→the capacitor C) via the current source DS2. On the other hand, when the current value of the current source DS1 is greater, the improper path is formed as a path (the capacitor C→the switch SW4→the current source DS1→the diode D3→the resistor R→the capacitor C) via the current source DS1.

In any case, since the improper path includes one of the current source DS1 and the current source DS2, the current value is corrected to the stimulation current value determined by the current source DS1 or the current source DS2. Accordingly, only the improper current with the output current difference (within the margin of error) between the different current sources DS1 and DS2 flows in the circuit, whereby the balance of the stimulation current of the bipolar pulse output from the electrode 10 is maintained.

That is, even when the parasitic diode unique to the switch to be turned off is forward biased in inverting the polarity of the bipolar pulse and improper current flows in the circuit, the current value is corrected to a value which can maintain the positive and negative (+ and −) charge balance of the bipolar pulse through the use of the current adjusting circuit. As a result, a living tissue is suitably electrically stimulated, An example of the application pattern (the cathodic-first pattern) of a stimulation pulse in which negative current (−) is made to flow from the electrode 10 in the first pulse and positive (+) current is made to flow in the second pulse is described above. Otherwise, in the case of a stimulation pulse application pattern (the anodic-first pattern) in which positive (+) current is made to flow in the first pulse and negative (−) current is made to flow in the second pulse, the current sources are connected to the power source side and the ground side in which an improper path may be formed. Accordingly, even when the parasitic diode to be turned off is forward biased, it is possible to maintain the charge balance of the bipolar pulse. As a result, it is possible to electrically stimulate a living tissue under various stimulation conditions of the bipolar pulse.

Figure 2:
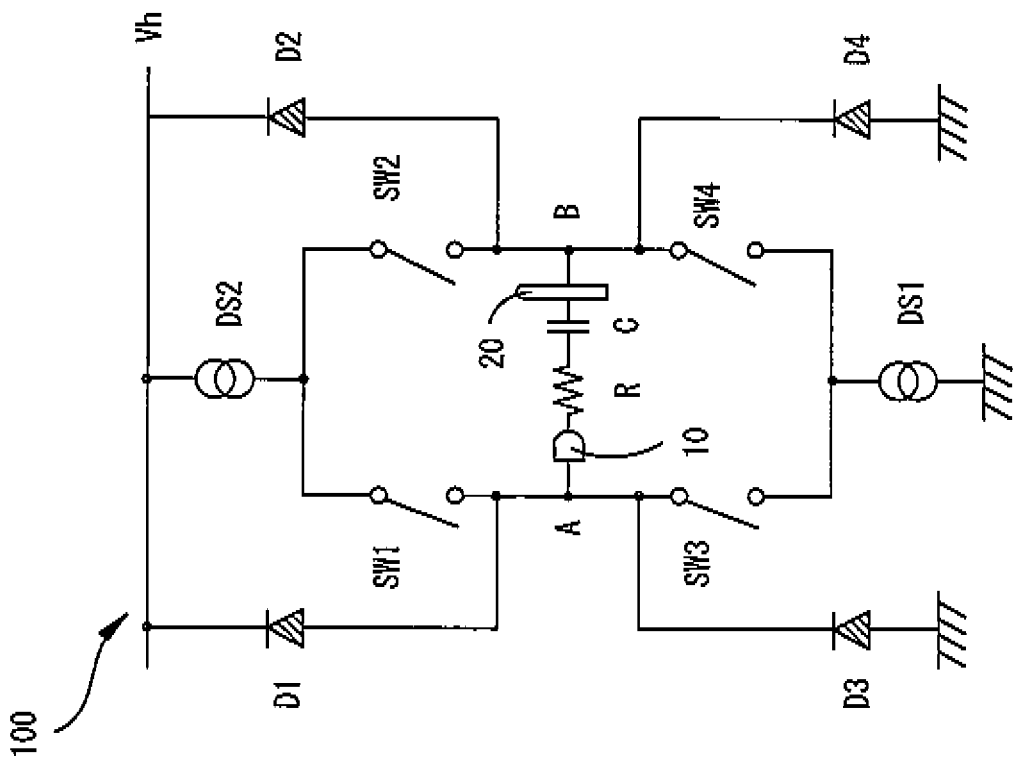
FIG. 2 is a diagram illustrating a second example of the stimulation circuit including a current adjusting circuit.

The configuration of the stimulation circuit including the current adjusting circuit is not limited to the above-mentioned. A stimulation circuit 100a according to a second example including a current adjusting circuit is shown in FIG. 2. In the below description, the same elements as in the stimulation circuit 100 are referenced by the same reference numerals. Here, it is assumed that the current value of the current source DS2 is greater than the current value of the current source DS1 within the margin of error of the stimulation current. In this case, there is a high possibility that an improper path is formed on the power source side connected to the current source DS2.

Therefore, in the stimulation circuit 100a according to the second example, a switch SW5 which is a bypass switch for switching the electrical connection of the current source DS2 is added to the stimulation circuit 100. Specifically, an end of the switch SW5 is connected to the power source Vh, the other end thereof is connected in series to the switch SW1 or SW2, and the current source DS2 and the switch SW5 which is a bypass switch are connected in parallel to the power source Vh.

By switching the ON and OFF states of the switch SW5, the current source DS2 is connected to the stimulation circuit 100a only when there is a possibility that an improper path is formed. Accordingly, it is possible to more efficiently utilize the voltage supplied from the power source Vh while controlling the improper current.

The operation of the stimulation circuit 100a will be described below. Here, it is assumed that the capacitor (capacitive component) C of a living body is not charged (does not have any potential) when outputting the first pulse. When the capacitor C is not charged in outputting the first pulse and a voltage is applied to the stimulation circuit 100a to output the first pulse, the potential of the output terminal A (B) is not higher than the potential of the power source Vh. In this case, since any improper path is not formed, the connection to the current source DS2 is not necessary. Therefore, the controller (not shown) turns on the switch SW5 in outputting the first pulse to cut off the electrical connection of the current source DS2 to the stimulation circuit 100a. Accordingly, a voltage is not applied to the current source DS2 in outputting the first pulse and the voltage supplied from the power source Vh is suitably used to output the stimulation current from the electrode 10.

On the other hand, when outputting the second pulse, the controller turns off the switch SW5 and electrically connects the current source DS2 to the stimulation circuit 100a. Accordingly, even when the polarity of the stimulation current is inverted in outputting the second pulse and an improper path is formed, the current value is suppressed without the margin of error of the stimulation current through the use of the current source DS2.

Sufficient stimulation current is output from the electrode 10 in the first pulse and thus the capacitor C is charged. When outputting the second pulse, the potential of the capacitor C serves as a power source, whereby the sufficient stimulation current is output from the electrode 10 in both the first pulse and the second pulse.

When a bipolar pulse is applied in the state where the capacitor C is charged in advance in outputting the first pulse, the absolute value of the maximum potential applied to the electrode 10 may be lowered and the load on the electrode 10 may be lowered. Therefore, by combination of the charging of the capacitor C and the stimulation condition of the bipolar pulse, the bipolar pulse may be output. In this case, a known potential difference detection circuit for detecting a potential is connected to the nodes A and B of the stimulation circuit 100a.

When it is determined that an improper current does not flow on the basis of the potential detection result on the nodes A and B (the capacitor C) using the potential difference detection circuit, the controller turns on the switch SW5 to electrically separate the current source DS2 from the circuit. On the other hand, when it is determined that an improper current flows, the controller turns off the switch SW5 to electrically connect the current source DS2 to the circuit. The bypass switch may be disposed in one or both of the current source DS1 and the current source DS2.

Figure 3:
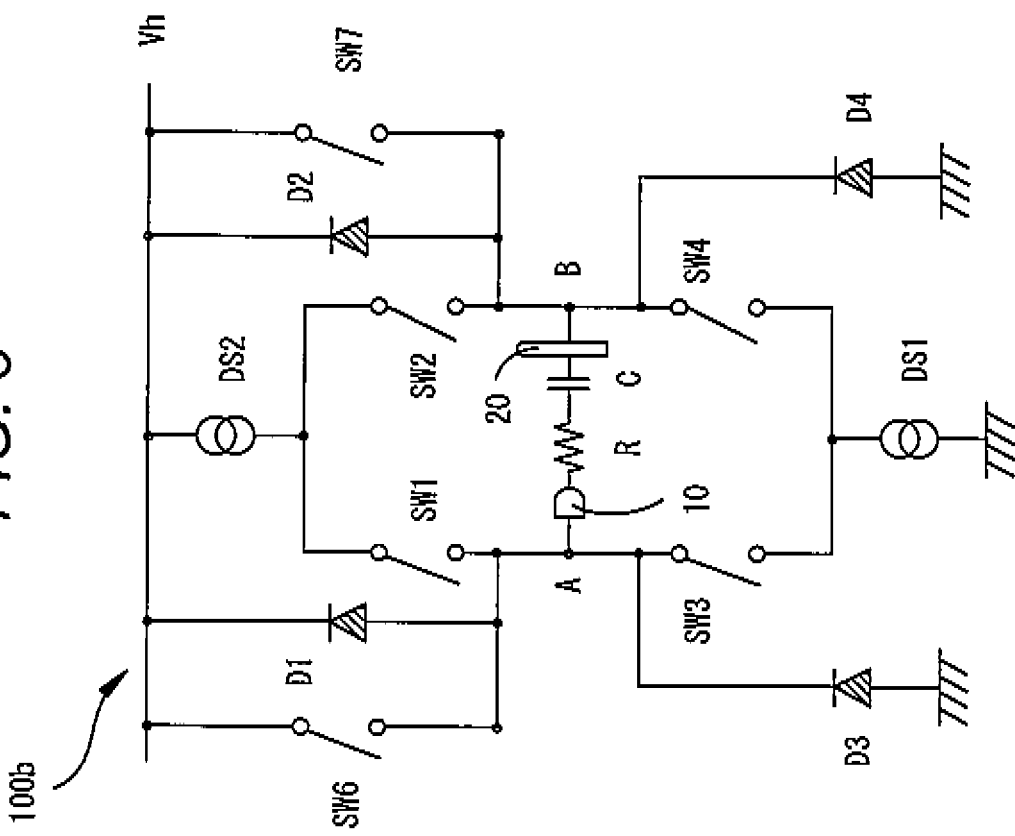
FIG. 3 is a diagram illustrating a third example of the stimulation circuit including a current adjusting circuit.

The configuration of a stimulation circuit 100b according to a third example including a current adjusting circuit is shown in FIG. 3. Here, switches SW6 and SW7 which are bypass switches capable of switching the connection of the current source DS2 to the stimulation circuit 100b are disposed instead of the switch SW5 which is a bypass switch in the stimulation circuit 100a according to the second example. Specifically, the switch SW6 is connected in parallel to the series connection of the current source D2 and the switch SW1. The switch SW7 is connected in parallel to the series connection of the current source DS2 and the switch SW2.

According to this configuration, when the first pulse is applied in the state where an improper current does not flow, for example, the controller turns on the switch SW7 and the switch SW3 which are opposed to each other and turns off the other switches. Accordingly, the current source DS2 used to control an improper current is electrically separated from the circuit and the voltage of the power source Vh is utilized suitably to output the stimulation current from the electrode 10.

On the other hand, when outputting the second pulse, the switch SW1 and the switch SW4 which are opposed to each other are turned on and the other switches are turned off. Accordingly, the current source DS2 is electrically connected to the stimulation circuit 100b to limit the improper current through the use of the current source DS2.

The electrical connection of the current source DS2 to the stimulation circuit is switched depending on the current polarity of the stimulation pulse, whereby the voltage of the power source Vh can be suitably used. Accordingly, this configuration is advantageous for the living tissue stimulation circuit requiring efficient use of a limited power source.

The stimulation circuit 100b can apply a bipolar pulse in the state where the capacitor C is charged in advance. For example, when outputting the first pulse, the opposing switches SW1 and SW4 are turned on and the other switches are turned off. Accordingly, the current source DS2 is electrically connected to the stimulation circuit 100b when outputting the first pulse. According to this configuration, even when the first pulse is applied in the state where the capacitor C is charged in advance and an improper current flows, the current value is limited through the use of the current source DS2.

In the stimulation circuit 100b, it may be detected through the use of a potential difference detection circuit whether the capacitor C is charged in outputting the first pulse and the ON and OFF states of the switches may be controlled by the controller. In the stimulation circuit 100b, since the switch SW6 and the switch SW7 are connected in parallel to the switches SW1 to SW4 of the H-bridged circuit, respectively, the resistance of the respective switches (SW1, SW2, SW6 and SW7) can be made to increase in comparison with the stimulation circuit 100a, whereby it is possible to easily simplify the configuration of the stimulation circuit 100b.

In an application of the stimulation circuit 100b, the switch SW6 and the switch SW7 which are bypass switches may be disposed on the current source DS1 side (the ground side). The bypass switches may be connected in parallel to both the current source DS2 side (the power source side) and the current source DS1 side (the ground side). In any case, the bypass switches are connected in parallel to the switches SW1 to SW4 of the H-bridged circuit and the current sources. The potential difference between the nodes A and B may be monitored through the use of a potential difference detection circuit and the ON and OFF states of the bypass switches may be controlled on the basis of the determination result on whether current flows in an improper path.

As described above, by disposing a current source (the current adjusting circuit) adjusting a current value in at least one of the power source side and the ground side in which an improper path of the stimulation circuit may be formed, the value of the improper current is limited by the current source even when the parasitic diode of a semiconductor switch to be turned off is forward biased, whereby the positive and negative (+ and −) charge balance of a bipolar pulse output from the stimulation circuit is maintained. Accordingly, even a stimulation condition of a bipolar pulse which could not be used in the circuit configuration according to the background art because the charge balance is broken down can be used in the stimulation circuit according to this example of the invention. Since the variation of the stimulation condition can be made to increase, various electrical stimulations can be applied to a living body.

Figure 4:
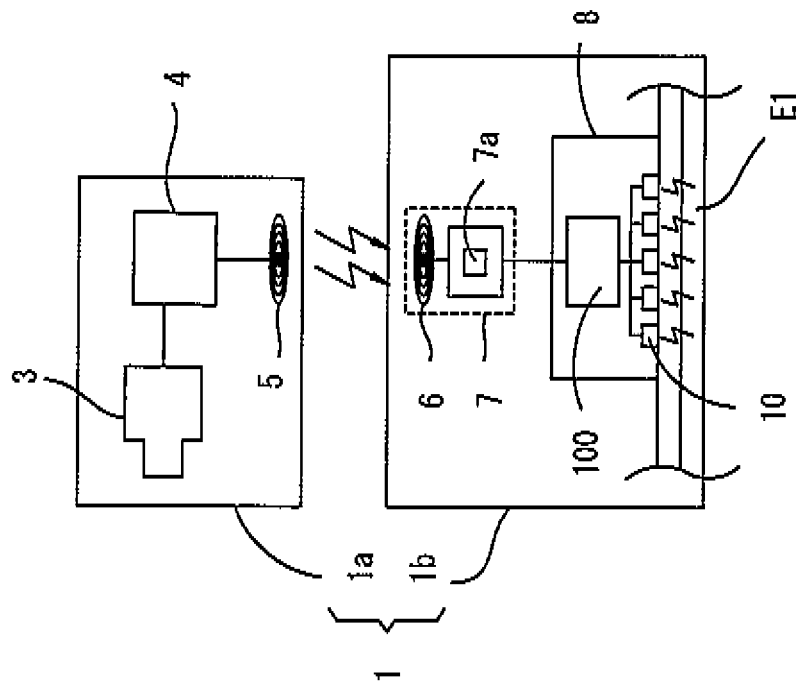
FIG. 4 is a block diagram illustrating a control system of a vision regeneration assisting apparatus.

An example in which a vision regeneration assisting apparatus regenerating a part or all of a patient's vision is used will be described as an example of the electrical stimulation device. FIG. 4 is a block diagram illustrating a control system of the vision regeneration assisting apparatus.

The vision regeneration assisting apparatus 1 includes an extracorporeal device 1a photographing an external system and an intracorporeal device 1b applying an electrical stimulation to cells of the retina to promote regeneration of a vision. The extracorporeal device 1a includes an imaging device 3 mounted on a visor (not shown) worn by a patent, an external device 4 converting a subject image captured by the imaging device 3 into image data and supplying power to the vision regeneration assisting apparatus 1, and transmission means 5 for transmitting the image data and power generated from the extracorporeal device 1a to the intracorporeal device 1b and being formed of a primary coil. A magnet (not shown) is disposed at the center of the transmission means 5 and is used to fix the position thereof relative to reception means 6 of the intracorporeal device 1b to be described later.

The intracorporeal device 1b includes reception means 6 for receiving the image data or power from the extracorporeal device 1a as electromagnetic waves, a receiving unit 7 including a controller 7a controlling the intracorporeal device 1b, a stimulator (stimulation unit) 8 applying an electrical stimulation to cells of the retina, and plural electrodes 10 connected to the stimulator 8. The stimulator 8 includes the above-mentioned stimulation circuit 100 (or 100a or 100b) and outputs a bipolar pulse from the electrode 10 on the basis of a control signal from the controller 7a. When the electrical stimulation is performed by the use of plural electrodes 10 as in this example, the plural electrodes 10 are switchably connected to a single stimulation circuit 100 so as to reduce the size of the device.

The operation of the vision regeneration assisting apparatus 1 will be described below. A subject image captured by the imaging device 3 is converted into image data by the external device 4 and is transmitted to the intracorporeal device 1b from the transmission means 5 as electromagnetic waves. In the intracorporeal device 1b, the image data and the power received by the reception means 6 is transmitted to the controller 7a. The controller 7a activates the stimulation circuit 100 on the basis of the received signal and outputs a bipolar pulse from the electrodes 10. Accordingly, the cells of the retina E1 of a patient's eye are stimulated and the patient obtains light sensitivity (vision).

At this time, in this example, even when an improper path is formed in the circuit depending on the stimulation condition of the bipolar pulse, the current value is suppressed within the margin of error of the stimulation current by the current source disposed on the power source side and the ground side. Accordingly, a bipolar pulse with a predetermined stimulation condition is precisely output from the electrodes 10. As a result, it is possible to enhance the variation of the stimulation condition, thereby providing various effects of vision regeneration to a patient.

In the above description, by disposing the current adjusting circuit in the living tissue stimulation circuit, the current value of an improper current flowing in the stimulation circuit can be controlled to enhance the variation of the stimulation condition. In addition, by adjusting the potential of the living tissue stimulation circuit so as for an improper current not to flow in the stimulation circuit, it may be possible to enhance the variation of the stimulation condition.

Figure 6:
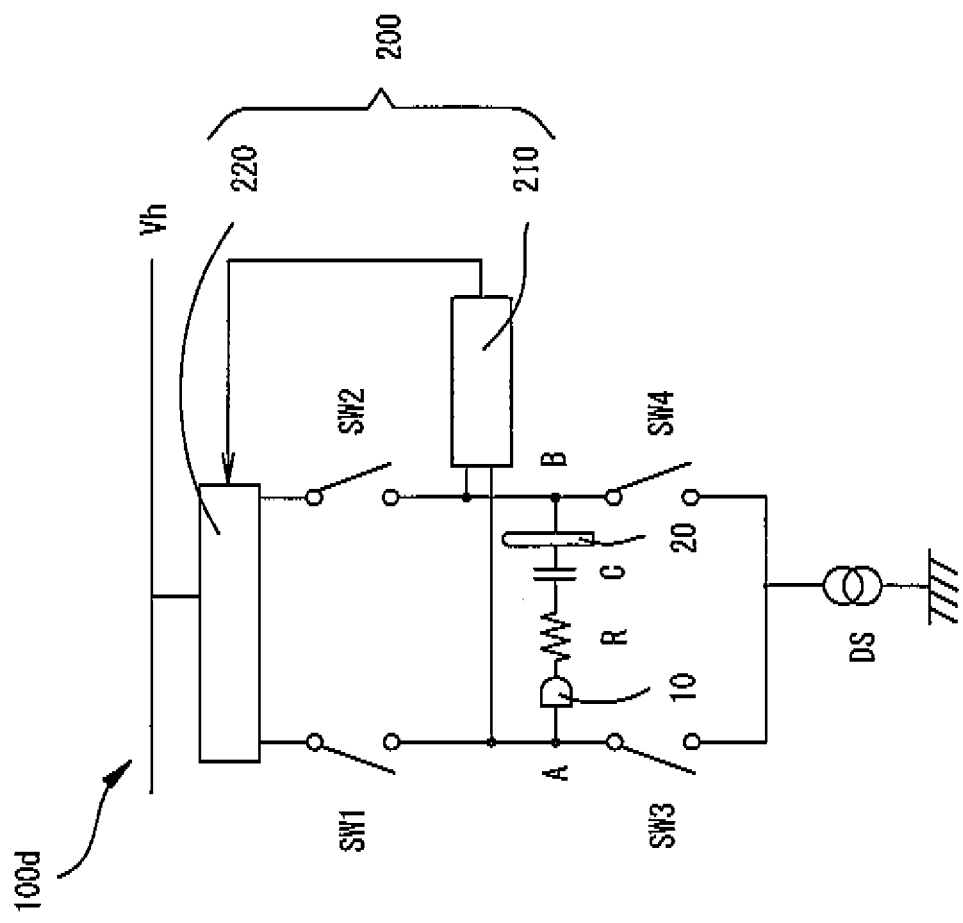
FIG. 6 is a block diagram illustrating a living tissue stimulation circuit including a potential compensation circuit.

FIG. 6 is a block diagram of the living tissue stimulation circuit including a potential compensation circuit. The same elements as in the living tissue stimulation circuit are referenced by the same reference numerals.

The stimulation circuit 100d includes the above-mentioned H-bridged circuit, an electrode 10 connected to the node A serving as an output terminal of the H-bridged circuit, a counter electrode 20 connected to the node B serving as another output terminal, and a potential compensation circuit 200.

Figure 24:
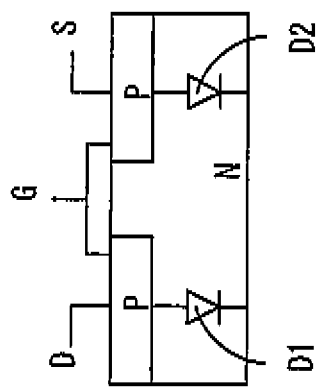
FIG. 24 is a diagram illustrating a parasitic PN junction.

The potential compensation circuit 200 includes a detection circuit 210 detecting the potential of at least one of the node A and the node B of the living tissue stimulation circuit and a voltage adjusting circuit 220 adjusting the potentials of the nodes A and B. The voltage adjusting circuit 220 adjusts the potential of at least one of the nodes A and B (or both the nodes A and B) on the basis of the detection result from the detection circuit 210, whereby the forward bias of the parasitic PN junction of a switch to be turned off is suppressed in switching the switches SW1 to SW4. (A diagram illustrating the parasitic PN junctions D1 and D2 included in the semiconductor switches is shown in FIG. 24).

In the H-bridged circuit (polarity switching circuit), an end of the switch SW1 and an end of the switch SW2 are connected in parallel to the power source (line) Vh, and an end of the switch SW3 and an end of the switch SW4 are connected in parallel to a DC current source DS disposed on the ground side.

As described above, a living tissue (not shown) disposed between the electrode 10 and the counter electrode 20 includes a resistive component and a capacitive component (generated by an electrical double layer) unique thereto. Although not shown, a resistor and a capacitor which are connected in series to determine an effective voltage range and to suitably cut off a DC component are connected between the node A and the electrode 10 and between the node B and the counter electrode 20. In FIG. 6, the resistive component and the capacitive component are expressed as an equivalent resistor R and an equivalent capacitor C.

The operation of the living tissue stimulation circuit including the potential compensation circuit will be described below. Here, a pulse in which current (negative (−) current) is made to flow in the stimulation electrode 10 via the living body from the counter electrode 20 at first (in the first pulse), then current (positive (+) current) is made to flow in the counter electrode 20 via the living body from the stimulation electrode 10 with the switched polarity (in the second pulse) will be exemplified as the bipolar pulse.

First, the combination of the switch SW2 and the switch SW3 is turned on and the combination of the switch SW1 and the switch SW4 is turned off in response to an instruction signal from a controller (not shown) connected to the stimulation circuit 100d. In this case, the node B becomes the potential of the power source Vh side and the node A becomes the potential of the ground side due to the current source DS. Accordingly, negative (−) stimulation pulse current (negative (−) current) is output from the electrode 10 (the first pulse). The capacitor C is charged with the negative (−) current to have a predetermined potential.

Then, by causing positive (+) current having the opposite polarity and the same amount of charge as the negative (−) current to flow, the controller switches the combination of the switch SW2 and the switch SW3 to the OFF state and switches the combination of the switch SW1 and the switch SW4 to the ON state. Accordingly, the node A becomes the potential of the power source Vh and the node B becomes the potential of the ground side due to the current source DS. Accordingly, positive (+) stimulation pulse current (positive (+) current) is output from the electrode 10 (the second pulse).

On the other hand, in inverting the polarity of the current output from the electrode 10, when the potential of the capacitor C charged with the first pulse remains, the potential of the node B which is the plus potential side of the capacitor C (which is connected to the power source Vh in outputting the first pulse) may be higher than the potential of the power source Vh. In this case, the parasitic PN junction of the switch to be turned off in outputting the second pulse is forward biased and improper current flows, whereby the charge balance of the current applied to the living tissue may be broken down.

Figure 20:
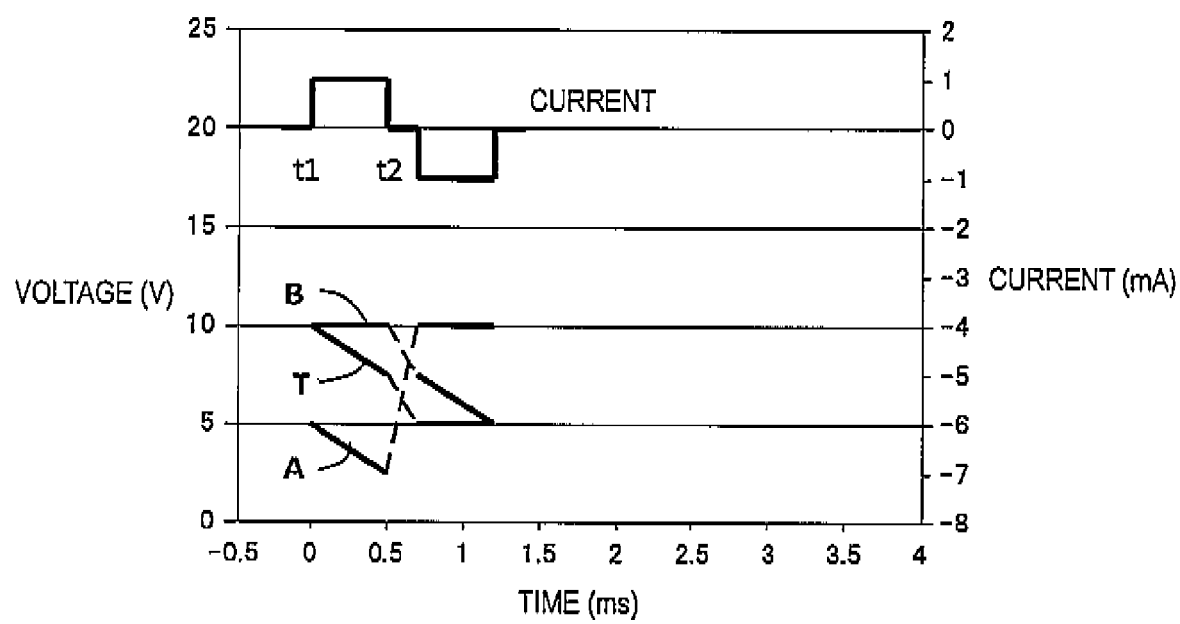
FIG. 20 is a diagram illustrating the relationship between the bipolar pulse current and the potential of a node in the stimulation circuit according to the background art.
Figure 21:
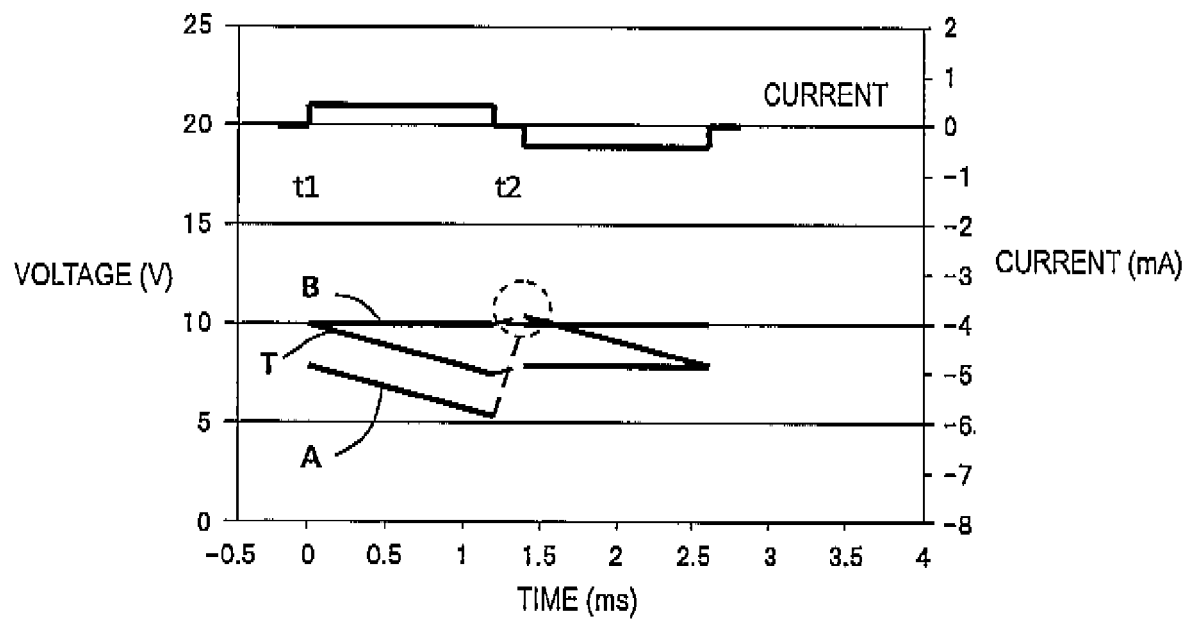
FIG. 21 is a diagram illustrating the relationship between the bipolar pulse current and the potential of a node in the stimulation circuit according to the background art.
Figure 22:
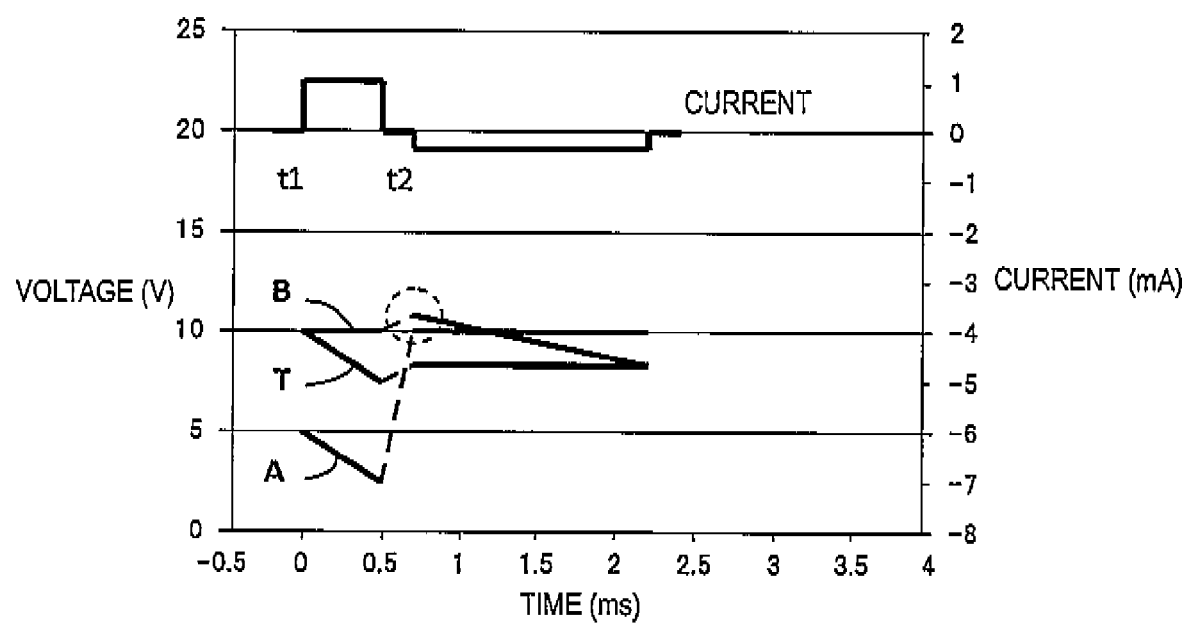
FIG. 22 is a diagram illustrating the relationship between the bipolar pulse current and the potential of a node in the stimulation circuit according to the background art.

FIGS. 20 to 22 show the variation in potential of the points (the nodes A and B and the living tissue T) when various stimulation conditions of the bipolar pulse is applied to the living tissue through the use of the stimulation circuit according to the background art not having the potential compensation circuit. Here, it is assumed that the potential of the power source Vh is set to 10 V.

In the stimulation condition of a bipolar pulse shown in FIG. 20, the potentials of the points (A, B, and T) are always suppressed to be equal to or lower than the potential (10 V) of the power source Vh. On the other hand, in the stimulation conditions of a bipolar pulse shown in FIGS. 21 and 22, it can be seen that the potential of the output terminal B is higher than the potential (10 V) of the power source Vh when switching the positive and negative (+ and −) polarities of the bipolar pulse (the corresponding part is indicated by a circle in the drawings). This is because the capacitor C has a charging potential due to the current of the first pulse of the bipolar pulse.

In this way, when the potential of the node B is higher than the potential of the power source Vh, the parasitic PN junction of the semiconductor switch (for example, the switch SW2) to be turned off is forward biased and thus unintentional improper current flows. Accordingly, the positive and negative (+ and −) charge balance of the bipolar pulse signal is broken clown and the charge left in the living body remains in the capacitive component caused by the electrical double layer. When the charge is stored in the capacitor, the electrolysis of body fluids is caused, which negatively affects the patient's living tissue.

Particularly, when plural electrodes 10 are connected to the living tissue stimulation circuit, plural electrodes 10 are often switchably connected to a single stimulation circuit to reduce the size of the device. In this case, a bipolar pulse is output from a certain electrode 10 and then the electrode is separated from the stimulation circuit. Accordingly, the path for discharging the charge accumulated in the capacitive component caused by the electrical double layer is cut and the surplus charge easily remains in the living body.

The capacitive component caused by the electrical double layer varies depending on the electrodes. Accordingly, in the stimulation device according to the background art, it is necessary to limit the degree of freedom of the stimulation condition of the bipolar pulse for the purpose of maintaining the positive and negative (+ and −) charge balance of all the electrodes in consideration of the capacitance of the capacitive component varying depending on the electrodes.

On the other hand, in this example, the detection circuit 210 is connected to the node side (that is, the node side connected to the power source Vh in outputting the first pulse) of which the potential may be higher than the potential of the power source Vh and monitors (detects) the potential of the node. The potential of the node is adjusted through the use of the voltage adjusting circuit 220 on the basis of the detection result so that the potentials of the nodes are not higher than the potential of the power source Vh.

The example where the negative (−) current is made to flow in the first pulse and the positive (+) current is made to flow in the second pulse is described above. However, even when the positive (+) current is made to flow in the first pulse and the negative (−) current is made to flow in the second pulse, the detection circuit 210 detects the potential of the node side (the plus potential side of the capacitor C) connected to the power source Vh in outputting at least the first pulse and the voltage adjusting circuit 220 adjusts the potentials of the nodes so as not to be higher than the voltage Vh on the basis of the detection result. Accordingly, the stimulation condition range of a bipolar pulse can be widened regardless of the order of applying the positive (+) charge and the negative (−) charge of the bipolar pulse.

Figure 7:
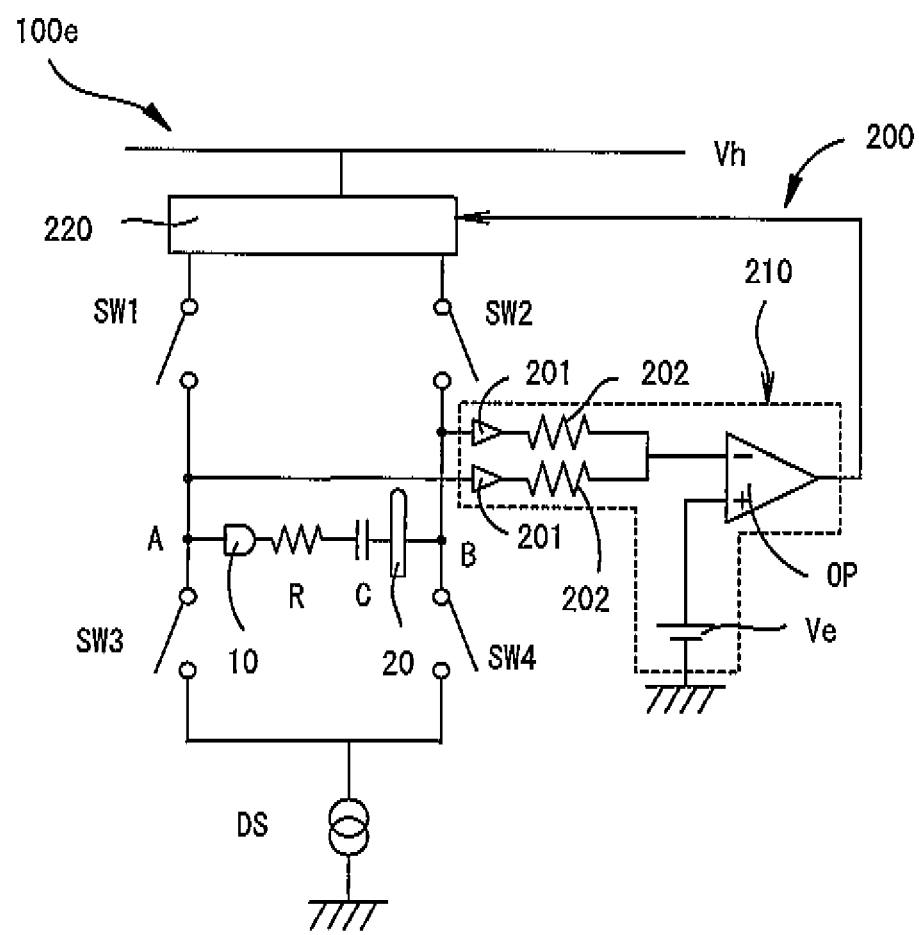
FIG. 7 is a diagram illustrating a first example of the stimulation circuit including a potential compensation circuit.

A specific example of the stimulation circuit having the potential compensation circuit will be described below. FIG. 7 shows a first example of the stimulation circuit 100*e* having the potential compensation circuit. The detection circuit 210 includes two pairs of a buffer 201 and a resistor 202, a reference power source Ve for determining a reference potential, and an operational amplifier OP for comparing the average potential of the nodes A and B with the potential of the reference power source Ve. Specifically, the buffer 201 and the resistor 202 are connected in series to the nodes A and B, the ends of two resistors 202 are connected to each others the output of the connection point thereof is input to the operational amplifier OP, and the output of the reference power source Ve is input to the operational amplifier OP.

The buffer 201 serves to suppress the flowing of current between the nodes A and B via two resistors 202 and to properly extract the voltage. Here, by setting the resistance values of the resistors 202 to the same, the average voltage of the nodes A and B is input to the operational amplifier OP. A known voltage adjusting circuit such as a MOS transistor, a bipolar transistor, and a switching control circuit is used in the voltage adjusting circuit 220.

Figure 8:
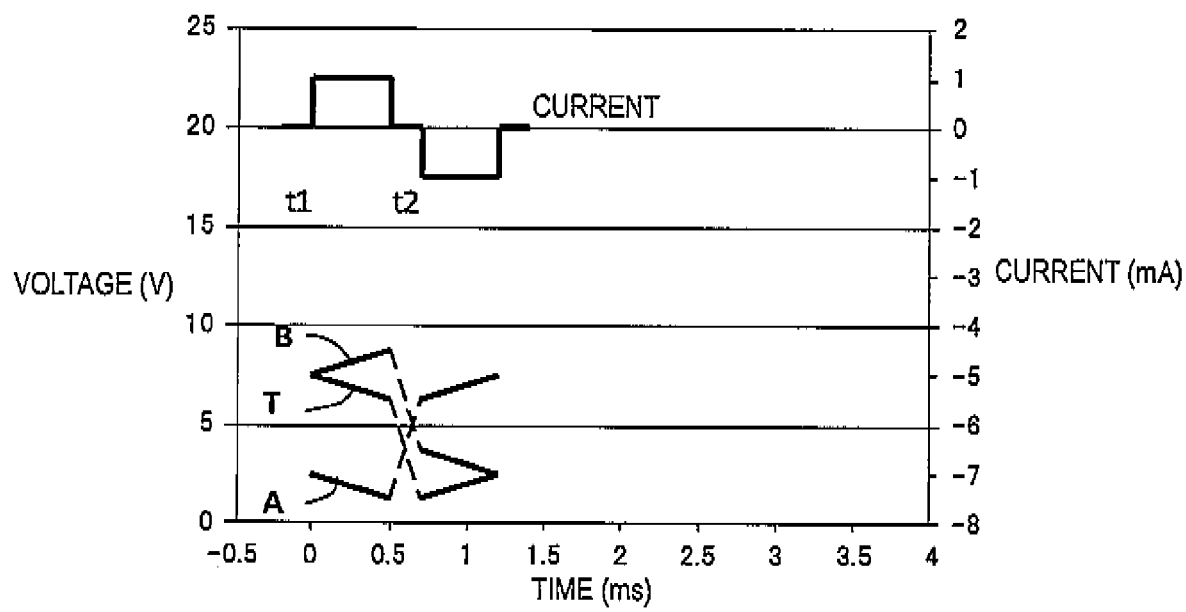
FIG. 8 is a diagram illustrating the relationship between the bipolar pulse current and the potential of a node in the stimulation circuit including the potential compensation circuit according to the first example.
Figure 9:
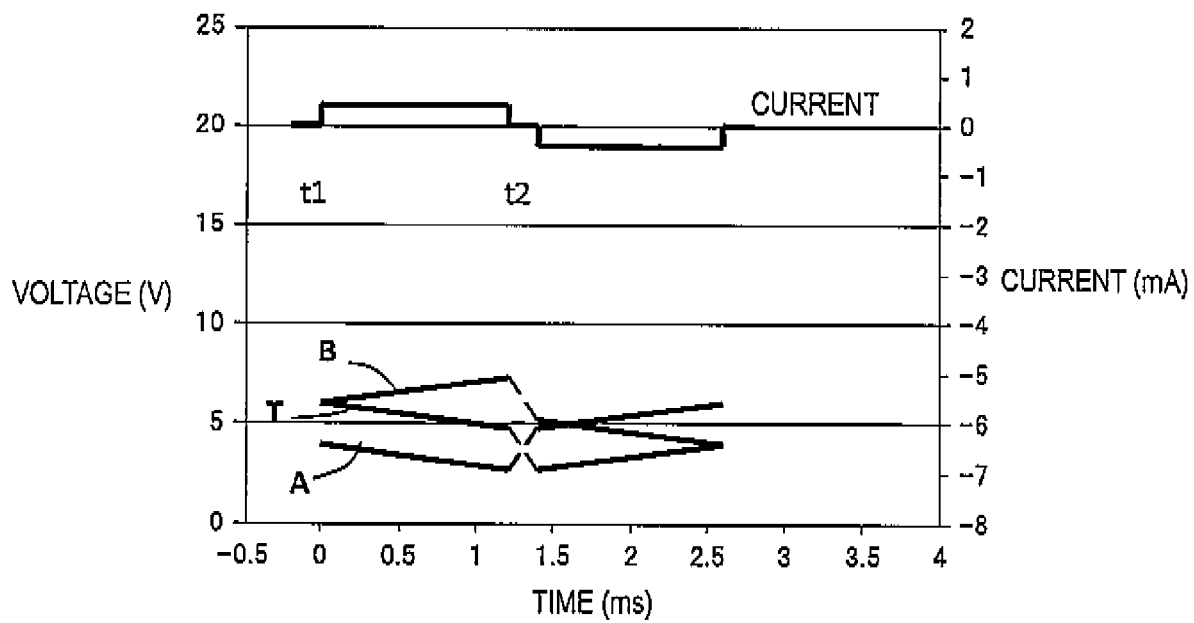
FIG. 9 is a diagram illustrating the relationship between the bipolar pulse current and the potential of a node in the stimulation circuit including the potential compensation circuit according to the first example.
Figure 10:
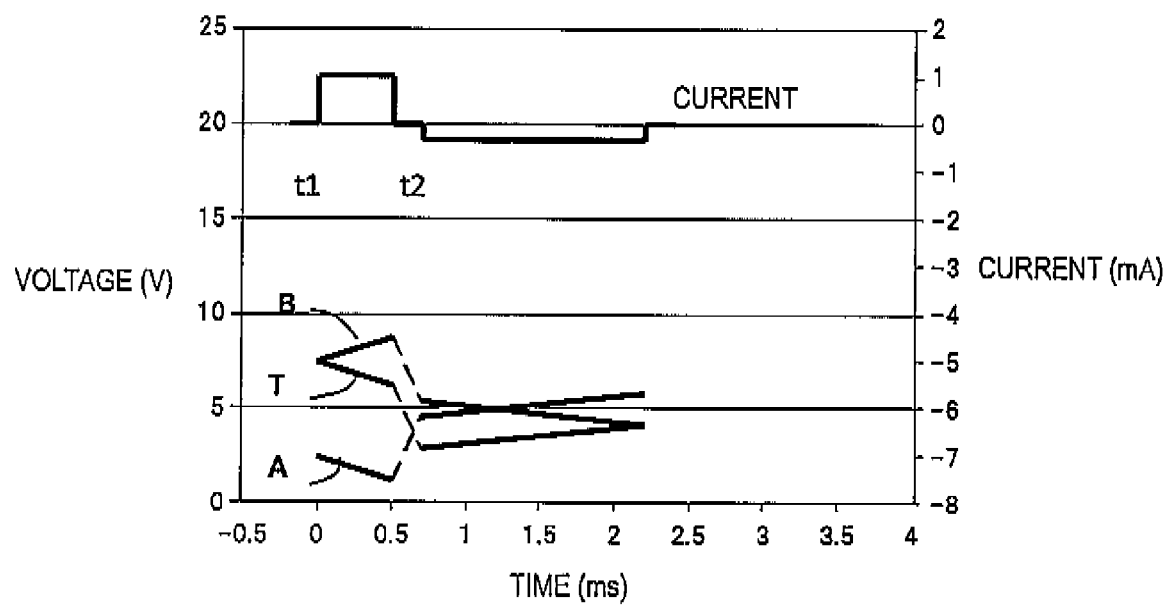
FIG. 10 is a diagram illustrating the relationship between the bipolar pulse current and the potential of a node in the stimulation circuit including the potential compensation circuit according to the first example.

Here, FIGS. 8 to 10 show the simulation result of the current of a bipolar pulse and the potential variation of the nodes A and B corresponding thereto when different stimulation conditions are applied using the stimulation circuit 100*e* (also shows the potential T of the living body). It is assumed that the voltage of the power source Vh is set to 10 V and the voltage of the reference power source Ve is set to 5 V.

With the operation of the stimulation circuit 100*e*, when negative (−) current is output from the electrode 10 between time t1 and time t2, the capacitor C is gradually charged with the charging potential. At time t2, the polarity of the current output from the electrode 10 is inverted to the positive (+) current by the switching operation of the stimulation circuit 100. During the operation, the average voltage V of the nodes A and B is compared with the potential of the reference power source Ve by the operational amplifier OP.

When it is detected by the operational amplifier OP that the average voltage V is higher than the potential of the reference power source Ve, the voltage adjusting circuit 220 adjusts the voltage from the power source Vh so as to lower the potentials of the nodes A and B and to make the average voltage of the node A and the node B close to the potential of the reference power source Ve. When the average voltage V is lower than the potential of the reference power source Ve, the voltage adjusting circuit 220 adjusts the voltage from the power source Vh so that the average potential V is made to be close to the potential of the reference power source Ve (the voltages of the nodes A and B are raised).

In this way, the potentials of the terminal A and the terminal B vary with respect to the reference power source Ve and thus the potentials of the nodes are in the range not higher than the potential of the power source Vh in spite of the charging potential of the capacitor C. It is also possible to widen the effective voltage range of the nodes A and B.

By disposing the potential compensation circuit 200 including a feedback circuit in the stimulation circuit 100*e* the potentials of the nodes are prevented from being higher than the potential of the power source Vh in switching the polarity regardless of the stimulation condition of the bipolar pulse. Accordingly, when the switches of the H-bridged circuit are turned off, it is prevented that the parasitic PN junction is forward biased to cause current to flow and charge is accumulated in the capacitive component caused by the electrical double layer. The variation of the stimulation condition of the bipolar pulse can be made to increase.

In the above description, the reference voltage Ve is set to 5 V, but the reference potential Ve is determined by the combination of the resistance values of two resistors 202. That is, the potentials of the nodes are determined not to be higher than the potential of the power source Vh.

The potential compensation circuit 200 is not limited to the above configuration. For example, the detection circuit 210 may be constructed by a known maximum potential detection circuit. For example, the maximum potential detection circuit is constructed by a source follower circuit or the like. In this case, the detection circuit (the maximum potential detection circuit) 210 detects the higher potential of the potentials of the node A and the node B and inputs the detected potential to the operational amplifier OP. On the other hand, the operational amplifier OP starts the comparison of the input voltage from the detection circuit 210 with the potential of the reference power source Ve, as described above.

At this time, when the output of the detection circuit 210 is higher than the reference power source Ve, the voltage adjusting circuit 220 adjusts the potential supplied from the power source Vh to decrease so that the higher potential of the nodes A and B is not higher than the reference power source Ve. In this way, the potentials of the terminals A and B are always adjusted to be equal to or lower than the reference power source Ve.

Figure 11:
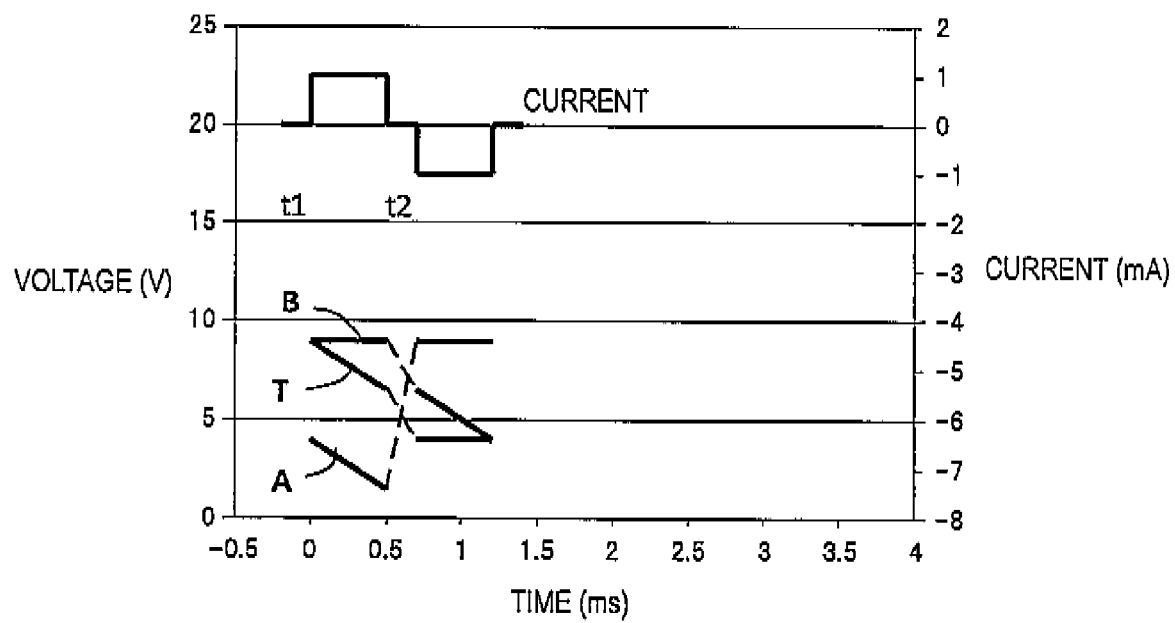
FIG. 11 is a diagram illustrating the relationship between the bipolar pulse current and the potential of a node when the potential compensation circuit includes a maximum potential detection circuit.
Figure 12:
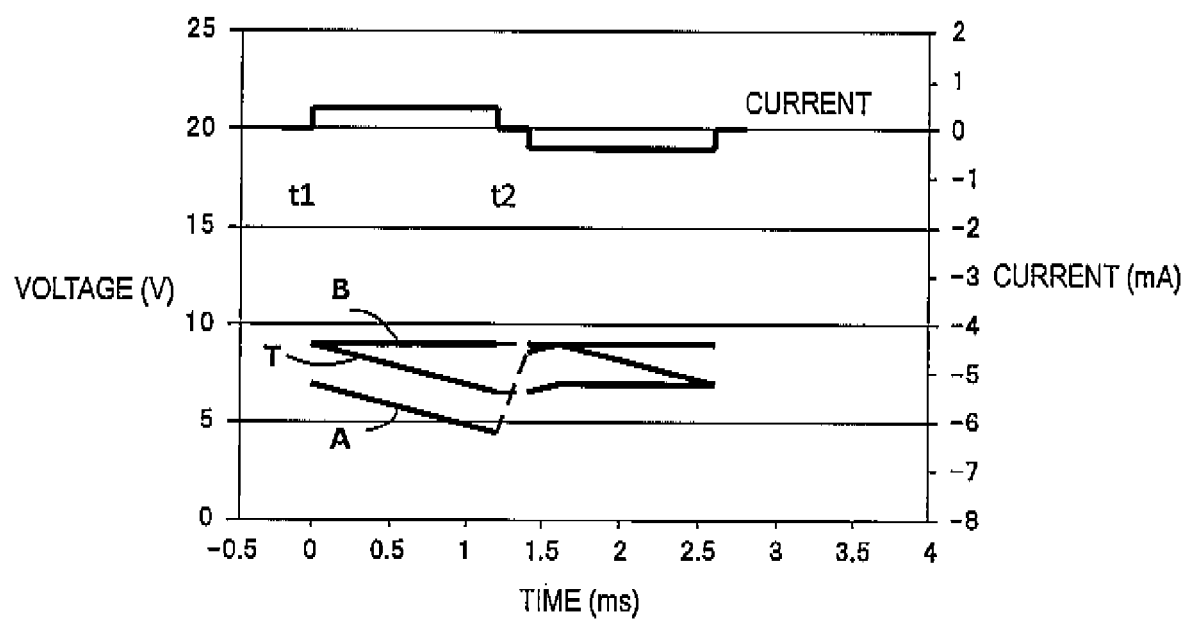
FIG. 12 is a diagram illustrating the relationship between the bipolar pulse current and the potential of a node when the potential compensation circuit includes a maximum potential detection circuit.
Figure 13:
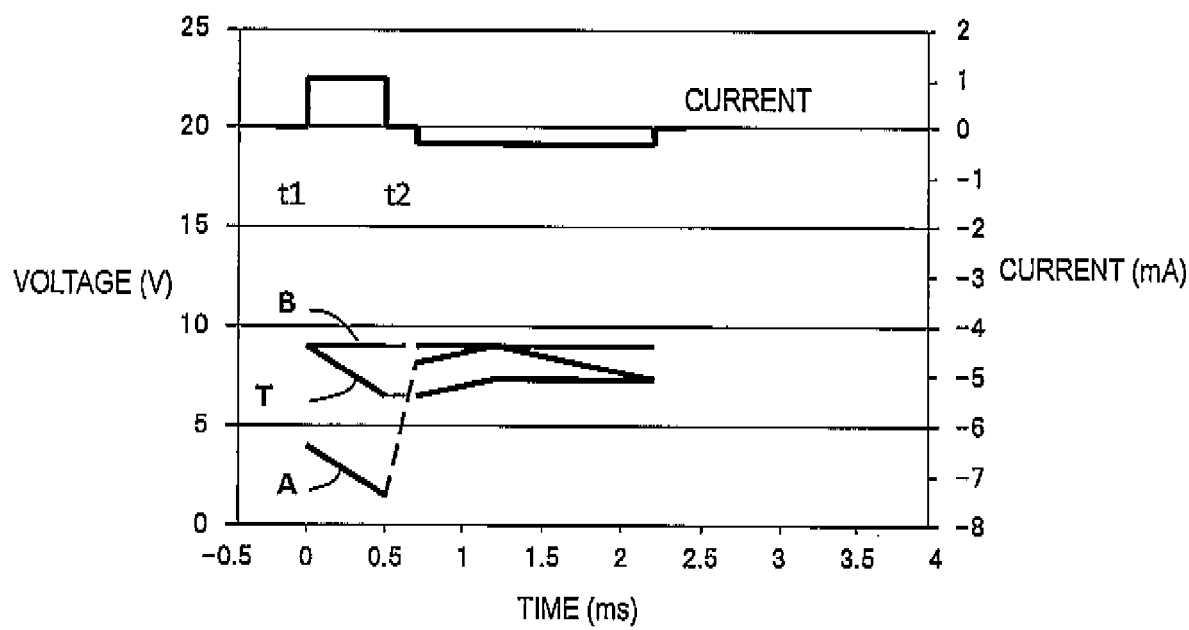
FIG. 13 is a diagram illustrating the relationship between the bipolar pulse current and the potential of a node when the potential compensation circuit includes a maximum potential detection circuit.

FIGS. 11 to 13 show diagrams when the potential compensation circuit includes the maximum potential detection circuit. Here, the simulation results of the bipolar pulse current and the potential, variations of the nodes A and B corresponding thereto are shown when the detection circuit 210 is constructed by the maximum potential detection circuit and different stimulation conditions are applied. It is assumed that the voltage of the power source Vh is set to 10 V and the reference voltage Ve is set to 9 V.

In this case, the potentials of the nodes A and B are always limited to be equal to or lower than the reference voltage Ve (9 V) and thus the potential of the node A or B is prevented from being higher than the potential of the power source Vh in switching the polarity of the bipolar pulse. Accordingly, the charge balance with the application of a bipolar pulse is maintained.

The above-mentioned two kinds of potential compensation circuits 200 can cope with both the case where the polarity of the bipolar pulse is switched from the positive (+) current to the negative (−) current and the case where the polarity of the bipolar pulse is switched from the negative (−) current to the positive (+) current. Accordingly, the order of the positive and negative (+ and −) polarities can be included in the variation of the stimulation condition and thus the bipolar pulse can be utilized in more stimulation conditions.

When the potential compensation circuit 200 is constructed by a feedback circuit and the stimulation condition of the bipolar pulse is determined to only one of the switching from the positive (+) current to the negative (−) current and the switching from the negative (−) current to the positive (+) current, the following configuration may be employed. In this case, it is possible to further simplify the configuration of the living tissue stimulation circuit 100.

Figure 14:
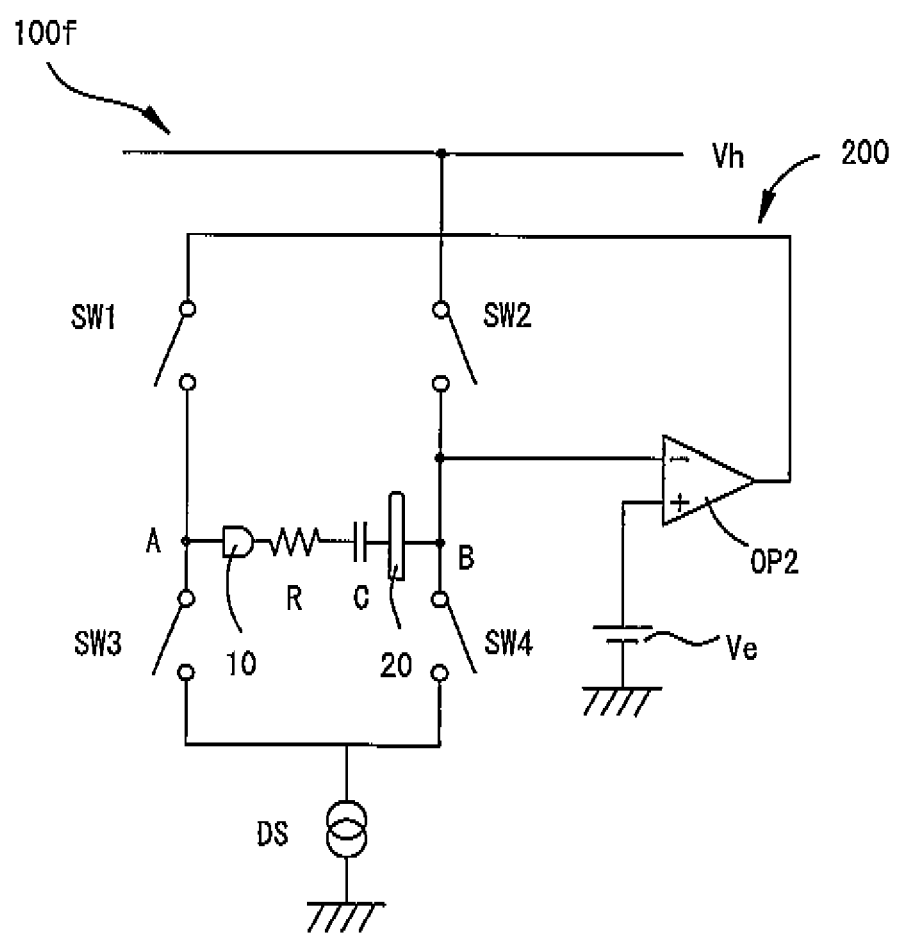
FIG. 14 is a diagram illustrating a second example of the stimulation circuit including a potential compensation circuit.

FIG. 14 shows a second example of the stimulation circuit including the potential compensation circuit. The detection circuit 210 of the stimulation circuit 100f includes an operational amplifier (a differential amplifier circuit) OP2 and a reference power source Ve. The operational amplifier OP2 serves as the potential adjusting circuit 220. It is assumed that a bipolar pulse with the negative (−) current in the first pulse and the positive (+) current in the second pulse is output from the electrode 10.

In this case, the node B which is connected to the power source (which is the plus potential of the charged capacitor C) is connected to the negative (−) input side ("−" side in FIG. 14) of the operational amplifier OP2 when applying the first pulse. The output of the reference potential Ve is connected to the positive (+) input side ("+" side in FIG. 14). During the application of the first pulse, since the potential Vh higher than the potential Ve of the positive (+) input side is applied to the (−) input side of the operational amplifier OP2, the operational amplifier OP2 outputs the maximum drivable potential to the switch SW1.

When the polarity of the current of the bipolar pulse is inverted, the operational amplifier OP2 extracts (amplifies) the difference between the potential of the node B and the reference potential Ve and controls the input voltage of the node A side so that the potentials are equal to each other. Accordingly, when the potential of the node B is higher than the reference potential Ve and the difference from the power source potential Vh decreases (when there is a high possibility that it is higher than the power source Vh), the input voltage of the node A side is adjusted to be lower and the potential of the node B can approach the potential of the reference voltage Ve.

On the other hand, when the potential of the node B is lower than the reference potential Ve, the input voltage of the node A side increases within the range where the operational amplifier OP2 can be driven and thus the potential of the output voltage B can approach the potential of the reference power source Ve. Accordingly, the potential of the node B which may be higher than the potential of the power source Vh is adjusted to a constant value (to approach the reference potential Ve).

Figure 15:
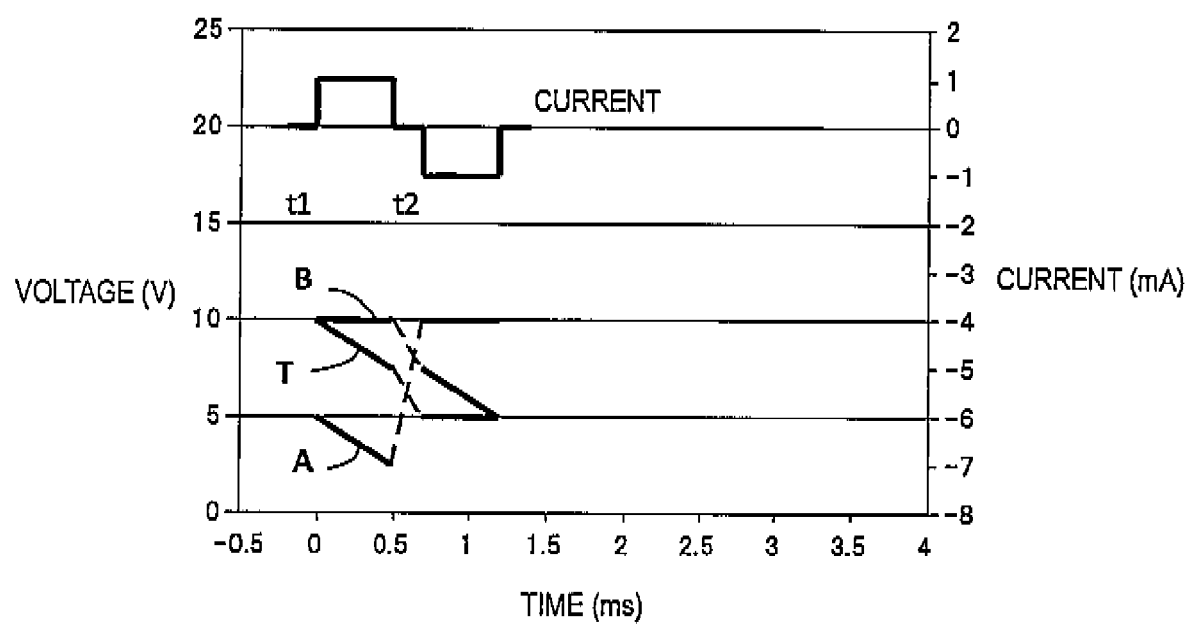
FIG. 15 is a diagram, illustrating the relationship between the bipolar pulse current and the potential of a node in the stimulation circuit according to the second example.
Figure 16:
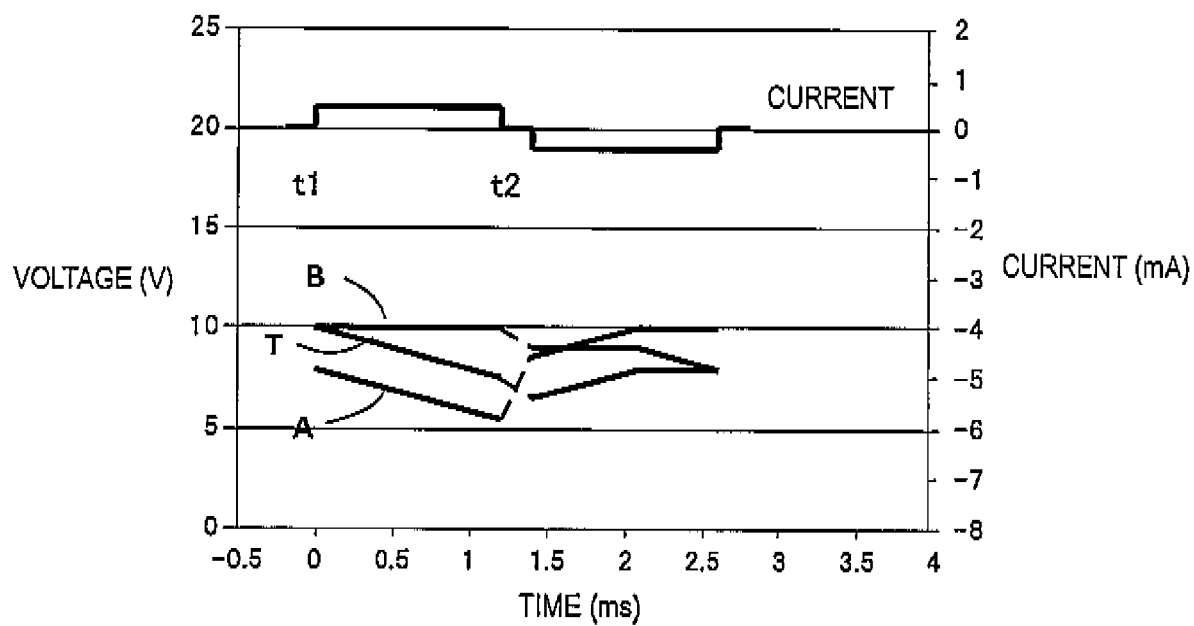
FIG. 16 is a diagram illustrating the relationship between the bipolar pulse current and the potential of a node in the stimulation circuit according to the second example.
Figure 17:
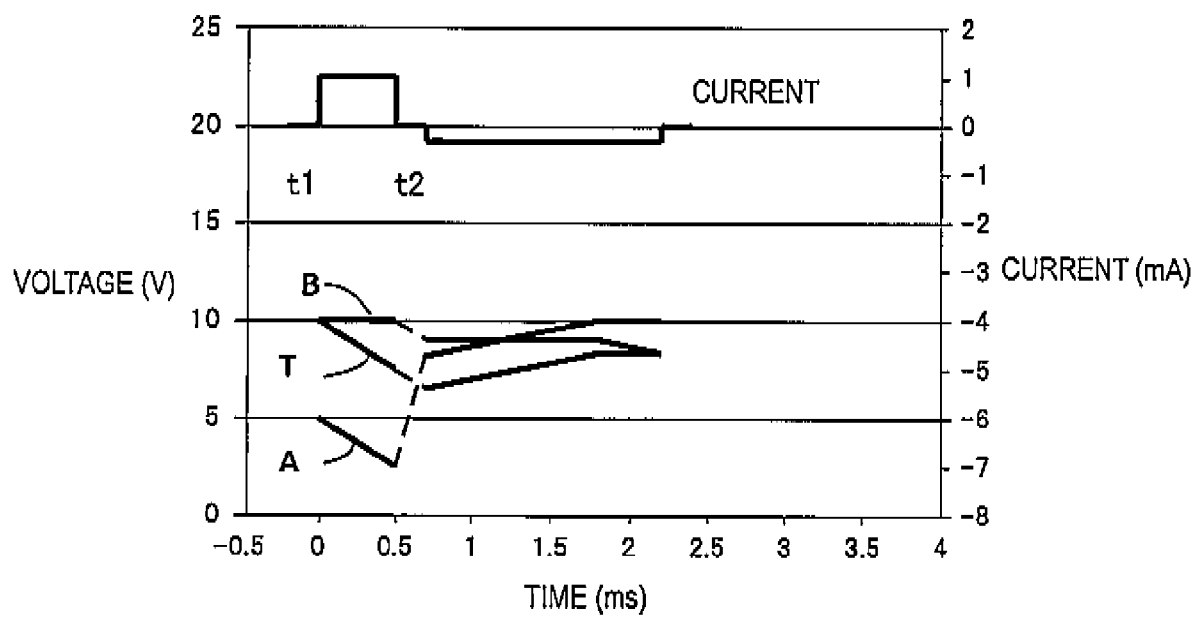
FIG. 17 is a diagram illustrating the relationship between the bipolar pulse current and the potential of a node in the stimulation circuit according to the second example.

FIGS. 15 to 17 are diagrams illustrating the relationship between a bipolar pulse and the potential of a node when the stimulation circuit 100f is employed and show the simulation results of the bipolar pulse and the potential variation of the nodes A and B corresponding thereto when difference stimulation conditions are applied. It is assumed that the reference potential Ve is set to 9 V.

It can be seen from the simulation result that the potentials of the nodes A are not higher than the potential of the power source Vh in inverting the current polarity in any stimulation condition of the bipolar pulse. Therefore, by disposing the above-mentioned feedback circuit, it is possible to enhance the variation of the stimulation condition of a bipolar pulse when the polarity of the bipolar pulse is determined as any one of the switching from the positive (+) current to the negative (−) current and the switching from the negative (−) current to the positive (+) current.

In this case, since the upper limit of the potential of the node A which is adjusted by the voltage adjusting circuit 220 (the operational amplifier OP2) is the range (the potential of the power source Vh) in which the operational amplifier OP2 can be driven, the potential of the node B which is detected by the detection circuit 210 may not reach the reference potential Ve. However, since it is prevented from being higher than the potential of the power source Vh, it is possible to perform the suitable electrical stimulation using various bipolar pulses.

Figure 18:
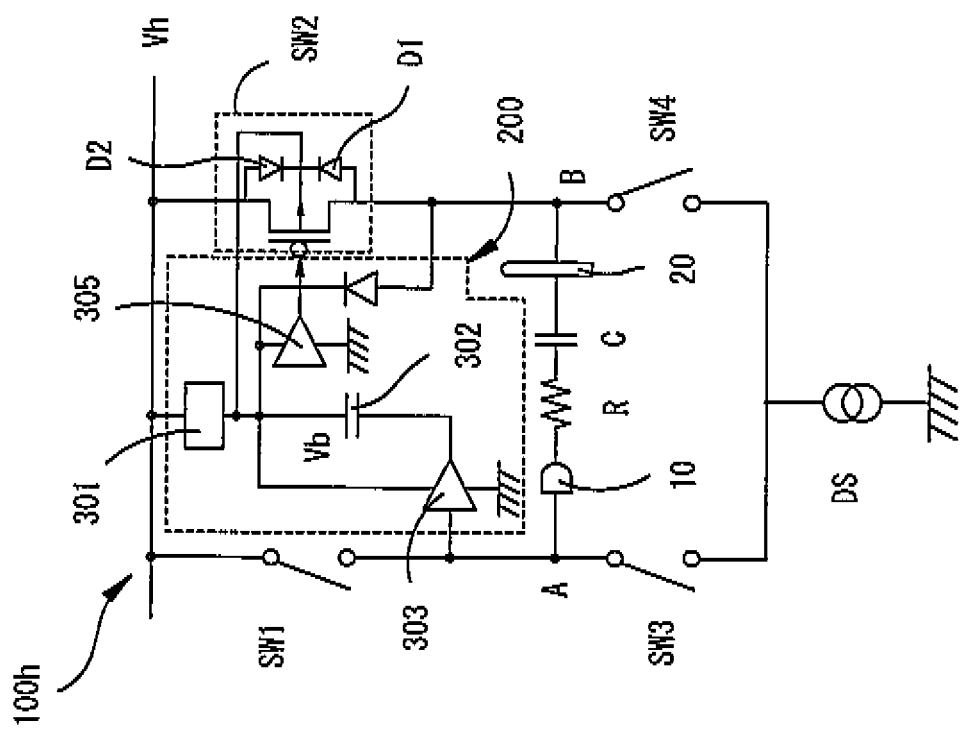
FIG. 18 is a diagram illustrating a third example of the stimulation circuit including a potential compensation circuit.

FIG. 18 shows a third example of the stimulation circuit having the potential compensation circuit. The detection circuit 210 of the stimulation circuit 100g includes an operational amplifier OP2 and a reference power source Ve. The switch SW1 serves as the potential adjusting circuit 220. In this case, the connection position of the gate terminal G of the (transistor) switch SW1 is switched between the terminal E of the power source Vh side and the terminal F of the output side of the operational amplifier OP2 depending on the timing of inverting the polarity of a bipolar pulse.

Specifically, in the first pulse in which negative (−) current is made to flow, the switch SW2 and the switch SW3 are turned on and the gate terminal G of the switch SW1 is connected to the terminal E. Accordingly, the resistance value between the source S and the drain D increases and thus the switch SW1 is turned off. The negative (−) current is output from the electrode 10 and thus the capacitor C is charged to a predetermined potential. At the timing of inverting the polarity of the bipolar pulse, the gate terminal G of the switch SW1 is switched to the terminal F. The comparison result of the potential of the node B with the potential of the reference power source Ve in the operational amplifier OP2 is given to the transistor constituting the switch SW1 and the voltage based on the difference between the potential of the node B and the reference potential Ve is added to the gate terminal G.

That is, when the potential of the node B is higher than the potential of the reference power source Ve (when the potential of the node B is close to the potential of the power source Vh), the potential of the gate terminal C is raised. Accordingly, the resistance value between the source S and the drain D of the switch SW1 is raised and the potential of the node A is lowered, whereby potential of the node B is lowered. As a result, the parasitic PN junction of the respective switches is prevented from being forward biased at the timing of inverting the polarity of the bipolar pulse.

The potential of the node is adjusted not to be higher than the potential of the power source Vh by disposing a feedback circuit as the potential compensation circuit 200, but the invention is not limited to this configuration. For example, the parasitic PN junction of the respective switches may be prevented from being forward biased by interlocking with the operation of the stimulation circuit.

Figure 19:
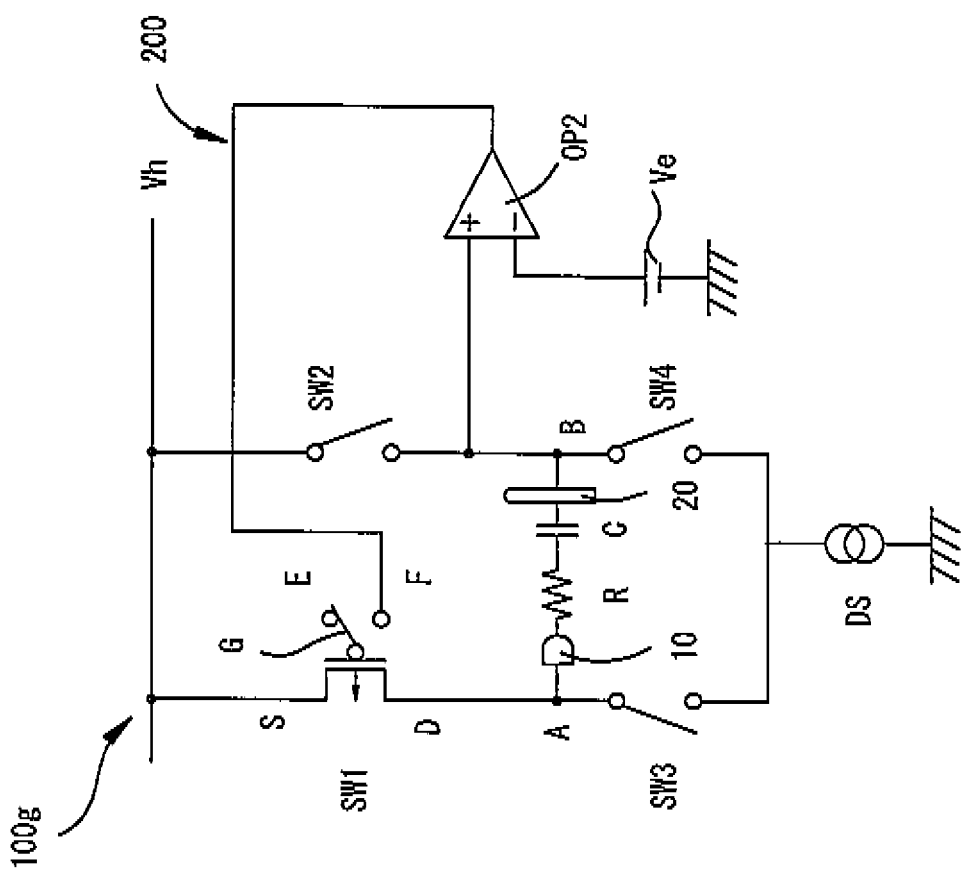
FIG. 19 is a diagram illustrating a fourth example of the stimulation circuit including a potential compensation circuit.

FIG. 19 shows a fourth example of the stimulation circuit including the potential compensation circuit. A bootstrap circuit is mounted as the potential compensation circuit 200 on the stimulation circuit 100$h$. The parasitic PN junction of the respective switches is prevented from being forward biased by interlocking with the operation of the stimulation circuit 100$h$.

Here, a rectifier circuit 301 (for example, a diode is used) is connected to the power source Vh and a bootstrap capacitor (hereinafter, referred to as a capacitor) 302 is connected to the other end of the rectifier circuit 301. The potential of the connection point between the rectifier circuit 301 and the capacitor 302 is connected to a back gate of the transistor constituting the switch SW2 and is also connected to the power source terminal of a driver 305 driving the gate of the switch SW2. On the other hand, the output of a buffer 303 blocking the inflow of current is connected to the other end of the capacitor 302 and the input of the buffer 303 is connected to the node A. For example, a source follower circuit including NMOS and PMOS transistors or the like is used for the buffer 303. Here, the configuration of the switch SW2 including the parasitic PN junctions D1 and D2 will be described in detail.

By employing the potential compensation circuit having the above-mentioned configuration, it is possible to generate a potential higher than the potential of the power source Vh through the use of the charging voltage of the capacitor 302. Accordingly, the parasitic PN junction of a semiconductor switch to be turned off can be prevented from being unintentionally forward biased.

The operation of the stimulation circuit 100$h$ will be described below. First, the switches SW2 and SW3 are turned on (the switches SW2 and SW4 are turned off) and thus the negative (−) current is output from the electrode 10. The capacitor C is charged with the DC current source DS and the potential of the node A is lowered due to the voltage drop in the resistor R. Accordingly, the capacitor 302 is charged to a predetermined potential (for example, a potential Vb) by the current flowing in, the rectifier circuit 301 connected to the power source Vh. At this time, the charging current of the capacitor 302 is prevented from flowing in a stimulation current path by the buffer 303.

Then, when the switches SW1 and SW4 are turned on (the switches SW2 and SW3 are turned off), the positive (+) current flows from the electrode 10 and the potential of the node A becomes the potential of the power source Vh by the switching, whereby the back gate potential of the switch SW2 is raised to Vb+Vh. Accordingly, even when the potential of the node B is higher than the potential of the power source Vh, the back gate potential of the switch SW2 connected to the capacitor 302 is raised sufficiently, whereby the parasitic PN junction of the switch SW2 is prevented from being unintentionally forward biased.

In this way, the positive and negative (+ and −) charge balance of a bipolar pulse is maintained with the driving operation of the stimulation circuit, whereby a living body can be properly electrically stimulated by the use of a bipolar pulse with various stimulation conditions.

The bootstrap circuit used as the potential compensation circuit 200 is not limited to this configuration. For example, the capacitor 302 may be charged using the parasitic PN junction (diode) D2 of the switch SW2 instead of the rectifier circuit (diode) 301 shown in FIG. 19. The switch SW2 includes a single PMOS transistor in FIG. 19. However, when the switch SW2 includes a series circuit of two PMOS transistors, the paths of the current flowing in the parasitic PN junctions of the switch SW2 (the PMOS transistors) are intercepted. Accordingly, when the parasitic PN junctions of the switch SW2 is forward biased and a parasitic bipolar transistor is provided, current is prevented from flowing to the outside. As a result, the charge balance of the bipolar pulse is properly maintained.

The stimulation circuits described above include the H-bridged circuit including four switches SW1 to SW4, but are not limited to this configuration. That is, the configuration is not particularly limited as long as the ON and OFF states of plural switches of the stimulation circuit are switched to output a bipolar pulse from the electrode 10.

Figure 23:
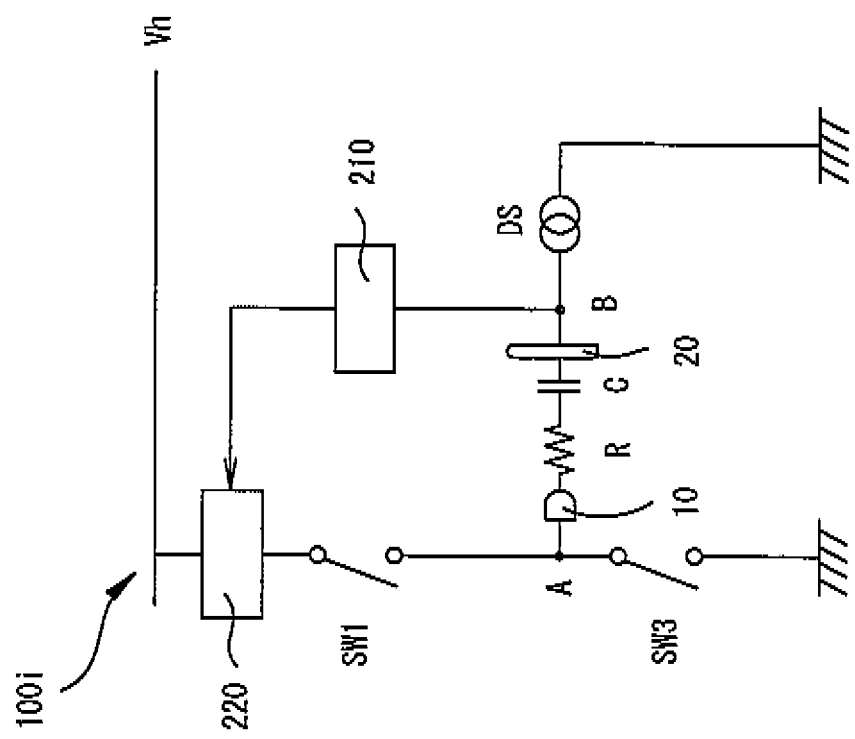
FIG. 23 is a diagram illustrating a fifth example of the stimulation circuit including a potential compensation circuit.

For example, as shown in FIG. 23 illustrating a fifth example of the stimulation circuit having a potential compensation circuit, the switch SW1 is connected to the power source Vh side of the stimulation circuit 100$i$, the switch SW3 is connected to the ground side, a voltage adjusting circuit 200 is connected between the switch SW1 and the power source Vh. The electrode 10 is connected to the connection position (the node A) of the switches SW1 and SW3. On the other hand, in the node B connected to the counter electrode 20, a bipolar DC current source DS switching the current polarity to both directions is connected between the node B and the ground side. The detection circuit 210 detecting a potential is connected to the node B and the output thereof is input to the voltage adjusting circuit 220. In this case, the direction of the current output from the bipolar DC current source DS is alternately switched in synchronization with the switching operation of the switches SW1 and SW3 and a bipolar pulse is output from the electrode 10.

For example, in the first pulse, the switch SW3 is turned ON and the switch SW1 is turned off, whereby the negative (−) current is output from the electrode 10. Then, in the second pulse, the switch SW1 is turned on and the switch SW3 is turned off, whereby the positive (+) current is output from the electrode 10. At this time, the voltage of the switch SW1 is adjusted by the voltage adjusting circuit 220 on the basis of the potential of the node B detected by the detection circuit 210, whereby the potential of the node B can be prevented from being higher than the potential of the power source Vh.

Various stimulation circuits 100d to 100i having the above-mentioned various potential compensation circuits are used in the vision regeneration assisting apparatus shown in FIG. 4, similarly to the stimulation circuit having the above-mentioned current adjusting circuit. Accordingly, the potential of the node (the electrode 10 or the counter electrode 20) of the stimulation circuit is adjusted not be higher than the potential of the power source Vh, regardless of the stimulation condition of a bipolar pulse. As a result, it is possible to enhance the variation of an electrical stimulation pulse, thereby giving various effects of vision regeneration to patients.

The configuration and the operation of the vision regeneration assisting apparatus using the stimulation circuit having the potential compensation circuit are the same as described above and thus detailed description thereof is not repeated.

The above-mentioned various living tissue stimulation circuits can be also used to electrically stimulate living tissues of various sites in a living body. Accordingly, the electrical stimulation of a living body can be carried out stably for a long period of time. For example, the configuration according to the invention can be applied to stimulation circuits embedded in a patient's living body for a long time and giving a predetermined electrical stimulation to the living body, such as an artificial middle ear providing an auditory sense to a patient and a heart pacemaker suppressing an occurrence of irregular heartbeat, whereby the stimulation condition range of a bipolar pulse can be widened and thus the electrical stimulation of a living body can be stably carried out for a long period of time.

What is claimed is:

1. A living tissue stimulation circuit comprising:
   an H-bridged circuit that includes a first series section in which a first semiconductor switch connected to a power source side and a third semiconductor switch connected to a ground side are connected to each other in series, and a second series section in which a second semiconductor switch connected to the power source side and a fourth semiconductor switch connected to the ground side are connected to each other in series, the first series section and the second series section being connected to each other in parallel;
   a stimulation electrode connected to a first node between the first semiconductor switch and the third semiconductor switch of the first series section;
   a counter electrode connected to a second node between the second semiconductor switch and the fourth semiconductor switch of the second series section;
   a capacitor disposed between the first node and the second node and configured to determine an effective voltage between the stimulation electrode and the counter electrode and cut off a direct component; and
   a current adjusting circuit including a first current source and a second current source which are configured to determine a current value output from the stimulation electrode, the first current source being disposed at an end of the ground side of the third semiconductor switch and an, end of the ground side of the fourth semiconductor switch and the second current source which is different from the first current source being disposed at an end of the power source side of the first semiconductor switch and an end of the power source side of the second semiconductor switch.

2. The living tissue stimulation circuit according to claim 1, wherein a bypass switch connected in parallel to the first current source or the second current source so as to bypass the first current source or the second source and the H-bridged circuit is disposed in at least one of the power source side and the ground side.

3. The living tissue stimulation circuit according to claim 2, wherein the bypass switch is connected in parallel to the first semiconductor switch and the third semiconductor switch or is connected in parallel to the second semiconductor switch and the fourth semiconductor switch.

4. The living tissue stimulation circuit according to claim 3, wherein, a combination of the first semiconductor switch and the fourth semiconductor switch and a combination of the second semiconductor switch and the third semiconductor switch of the II-bridged circuit are alternately turned on and off so as to switch positive and negative current polarities of a first pulse and a second pulse of a bipolar electrical stimulation pulse output from the stimulation electrode.

5. The living tissue stimulation circuit according to claim 4, wherein the current polarity of the bipolar electrical stimulation pulse signal is switched to any one of an anodic-first pattern in which positive current is output in the first pulse and negative current is output in the second pulse and a cathodic-first pattern in which negative current is output in the first pulse and positive current is output in the second pulse.

6. The living tissue stimulation circuit according to claim 5, wherein at least one of the bypass switches connected in parallel to the first current source and the second current source is turned on when the first pulse is output and is turned off when the second pulse is output.

7. The living tissue stimulation circuit according to claim 6 further comprising a potential difference detection circuit configured to detect a potential difference between the first node and the second node,
   wherein at least one of the bypass switches connected in parallel to the first current source and the second current source is turned on depending on the potential difference detected by the potential difference detection circuit.

8. A living tissue stimulation circuit comprising:
   an H-bridged circuit that includes a first series section in which a first semiconductor switch connected to a power source side and a third semiconductor switch connected to a ground side are connected to each other in series, and a second series section in which a second semiconductor switch connected to the power source side and a fourth semiconductor switch connected to the ground side are connected to each other in series, the first series section and the second series section being connected to each other in parallel;
   a stimulation electrode connected to a first node between the first semiconductor switch and the third semiconductor switch of the first series section;
   a counter electrode connected to a second node between the second semiconductor switch and the fourth semiconductor switch of the second series section;
   a capacitor disposed between the first node and the second node and configured to determine an effective voltage between the stimulation electrode and the counter electrode and cut off a direct component; and
   a potential compensation circuit configured to adjust the potential of at least one of the first node and the second node so as to satisfy a voltage range in which a parasitic PN junction of the semiconductor switch to be turned off is not forward biased.

9. The living tissue stimulation circuit according to claim 8, wherein the potential compensation circuit includes a detection circuit configured to detect the potential of at least one of the first node and the second node.

10. The living tissue stimulation circuit according to claim 9, wherein when the detection circuit is connected to both the first node and the second node, the detection circuit detects an average potential of the first node and the second node or a higher or lower potential of the potentials of the first node and the second node.

11. The living tissue stimulation circuit according to claim 10, wherein the potential compensation circuit is a bootstrap circuit.

12. The living tissue stimulation circuit according to claim 11, wherein the potential compensating circuit includes:
   a rectifier circuit connected to the power source side; and
   a capacitor connected to the rectifier circuit and one of the first semiconductor switch and the second semiconductor switch of the power source side, the capacitor being charged with the potential with one polarity of a bipolar pulse, and
   the charged potential of the capacitor becomes higher than the potential of the power source side due to the polarity inversion of the bipolar pulse and the first semiconductor switch or the second semiconductor switch is prevented from being forward biased due to the potentials of the first node and the second node.

* * * * *